United States Patent [19]

Gushima et al.

[11] 4,410,626

[45] Oct. 18, 1983

[54] PROCESS FOR THE PRODUCTION OF 7α-METHOXYCEPHALOSPORIN DERIVATIVES

[75] Inventors: Hiroshi Gushima, Ageo; Shunichi Watanabe, Omiya; Takeshi Saito, Tokyo; Toshio Sasaki, Toda; Hideo Eiki, Omiya; Yoshihiko Oka, Kawagoe; Takashi Osono, Tokyo, all of Japan

[73] Assignee: Yamanouchi Pharmaceutical Co. Ltd., Tokyo, Japan

[21] Appl. No.: 201,739

[22] Filed: Oct. 29, 1980

Related U.S. Application Data

[62] Division of Ser. No. 97,823, Nov. 27, 1979, Pat. No. 4,259,326.

[30] Foreign Application Priority Data

Dec. 12, 1978 [JP] Japan .................................. 53-153871

[51] Int. Cl.$^3$ ........................ C12P 35/08; C12N 9/06; C12R 1/465; C12R 1/52
[52] U.S. Cl. .................................... 435/48; 435/191; 435/886; 435/893; 435/897
[58] Field of Search ........................... 435/47, 48, 191

[56] References Cited

U.S. PATENT DOCUMENTS

| | | | |
|---|---|---|---|
| 3,719,563 | 3/1973 | Hamill et al. | 435/48 |
| 3,865,693 | 2/1975 | Arai et al. | 435/48 |
| 3,914,157 | 10/1975 | Stapley et al. | 435/48 |
| 3,974,035 | 8/1976 | Shonura et al. | 435/48 |
| 4,017,485 | 4/1977 | Hasegawa et al. | 435/48 |
| 4,039,660 | 8/1977 | Osono et al. | 435/47 |

*Primary Examiner*—Alvin E. Tanenholtz
*Attorney, Agent, or Firm*—Burgess, Ryan and Wayne

[57] ABSTRACT

7α-Methoxy-3-p-sulfooxy or p-hydroxycinnamoyloxymethyl cephalosporin derivatives which are useful as antibiotics and as intermediates for the production of other 7α-methoxycephalosporin derivatives.

10 Claims, 12 Drawing Figures

PROCESS FOR THE PRODUCTION OF 7α-METHOXYCEPHALOSPORIN DERIVATIVES

CROSS-REFERENCE TO RELATED APPLICATION

This application is a divisional of co-pending application Ser. No. 97,823, filed Nov. 27, 1979, now U.S. Pat. No. 4,259,326.

DETAILED EXPLANATION OF THE INVENTION

This invention relates to novel 7α-methoxycephalosporin derivatives and a process for the production thereof. These derivatives are useful as antibiotics for their high antibacterial activities and further they are useful as intermediates for producing other 7α-methoxycephalosporin derivatives.

In the field of cephalosporin chemistry, it is known that the compounds having a 7α-methoxy group have a merit that they maintain their antibiotic activities for a long period of time without losing the activities since they are resistant to β-lactamases and hence the usefulness of them is very high. As various kinds of 7α-methoxycephalosporin derivatives are obtained with the progress of studies on these derivatives and it becomes possible to apply effectively these derivatives to various infectious diseases which have hitherto been trated insufficiently, the development of 7α-methoxycephalosporin compounds having more effective activities has been demanded. In such circumstances, the compound having a 5-amino-5-carboxyvaleramido group or 4-carboxybutyramido group at the 7β-position and an α-methoxy-p-hydroxycinnamoyloxymethyl group or α-methoxy-p-sulfooxycinnamoyloxymethyl group at the 3-position (abbreviated as 810A in U.S. Pat. No. 3,914,157) and the compound having a 5-amino-5-carboxyvaleramido group or 4-carboxybutyramido group at the 7β-position and a heterocyclic thiomethyl group at the 3-position (Deutsch Offenlegungsschrift No. 2,657,599) are obtained by fermentation methods and although these compounds have excellent antibacterial activities, the development of compounds having far more excellent antibacterial activities has further been demanded.

As the results of various investigations, the inventors has discovered that the novel 7α-methoxycephalosporin derivatives having general formula I

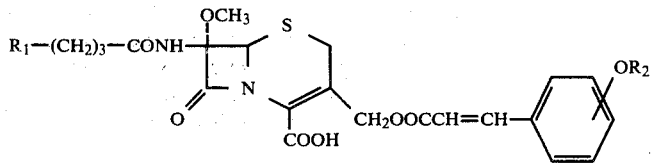

wherein $R_1$ represents a carboxy group or an α-aminocarboxymethyl group and $R_2$ represents a hydrogen atom or a sulfo group, have excellent antibacterial activities, in particular, antibacterial activities against gram negative bacteria, and have accomplished this invention based on the discovery.

The compounds of formula I have a characteristic feature in the point that they have a sulfooxy- or hydroxycinnamoyloxymethyl group at the 3-position and are useful as antibiotics. Also, the compounds of formula I are unexpectedly stable as compared with the above-described known compound 810A having an α-methoxy-p-sulfooxycinnamoyloxymethyl group or an α-methoxy-p-hydroxycinnamoyloxymethyl group at the 3-position thereof. Therefore, the isolation of the compounds of formula I from fermented broth and the purification of these compounds can be smoothly practiced without concurrence of the reduction in yield caused by the decomposition of the products during the steps of their isolation and purification.

Furthermore, the compounds of formula I have unexpectedly a merit that the stability of the cinnamoyloxymethyl group at the 3-poxition thereof in the steps of their isolation and purification does not disturb their conversion of the said group into a substituted-thiomethyl group at the 3-position by reacting the compounds with a thiol compound, for example, a heterocyclic thiol such as 1-methyltetrazole-5-thiol, 5-methyl-1,3,4-thiadiazole-2-thiol, etc. That is, various kinds of novel or known 7α-methoxycephalosporins can be produced in large quantities by first preparing 7α-methoxycephalosporin derivatives of formula I by the process of this invention as will be described later, then, converting the cinnamoyloxymethyl group at the 3-position into a substituted-thiomethyl group, and further introducing another acylamino group to the 7β-position thereof.

The 7α-methoxycephalosporin derivatives having a heterocyclic thiomethyl group at the 3-position can be obtained by the method of the above-mentioned Deutsch Offenlegungsschrift No. 2,657,599, but said method requires the investigation and modification of fermentation conditions according to the properties of thiol compound used in the fermentation. On the other hand, 7α-methoxycephalosporin compounds having various kinds of 3-substituted thiomethyl groups respectively can be easily produced in large quantities from the 7α-methoxycephalosporin derivatives of formula I which is more stable than the compound shown in U.S. Pat. No. 3,914,157 by converting the cinnamoyloxymethyl group at the 3-position into a desired substituted thiomethyl group by a chemical method.

It is worthy of special mention for such intermediates products that the substituents of the compounds of formula I at the 3-position and 7β-position of the cephalosporin nucleus can be easily converted into other various substituents by an ordinary chemical method. As the compounds induced from the compounds of formula I, there are series of cephalsporin derivatives having a 1-methyltetrazol-5-ylthiomethyl group at the 3-position and a 1,3,4-thiadiazol-2-ylthioacetamido group, a cyanomethylthioacetamido group, a trifluoromethylthioacetamido group, a {4-(carbamoyl carboxymethylene)-1,3-dithietan-2-yl}carboxamido group, a 4-carboxy-3-hydroxyisothiazol-5-ylthioacetamido group, etc., at the 7β-position. The conversion of the substituents at the 3-position and the 7β-position can be performed in any desired order.

The conversion of the substituent at the 3-position is accomplished by reacting the compound of formula I or the salt thereof or the 7β-substituted compound thereof with 1-methyltetrazole-5-thiol or an alkali metal salt thereof in water or an organic solvent such as acetone, dimethyl formamide, acetonitrile, methanol, ethanol, etc., or a mixed solvent thereof at about neutral state or alternatively in an anhydrous organic solvent in the presence of a boron trifluoride or a complex compound thereof. Also, the conversion of the substituent at the 7β-position can be performed by reacting the compound of formula I or the 3-substituted compound thereof first with a halogenating agent such as phosphorus pentachloride and then with a lower alcohol such as methanol at −50° C. to −20° C. in the presence of a base in an amount of 2.5–3.5 moles per mole of the halogenating agent to form a corresponding iminoether compound and then reacting the product with 1,3,4-thiadiazol-2-ylthioacetic acid, cyanomethylthioacetic acid, trifluoromethylthioacetic acid, 4-carboxy-3-hydroxyisothiazol-5-ylthioacetic acid, 4-(carbamoyl carboxymethylene)-1,3-dithietan-2-carboxylic acid, or a reactive derivative thereof.

According to this invention, the compounds of formula I are produced by the following manners.

(a). The compound of formula I wherein $R_1$ is an α-aminocarboxymethyl group

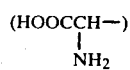

(hereinafter, referred to as compound $I_1$) is produced by cultivating 7α-methoxycephalosporin antibiotics producing strains belonging to the genus Streptomyces in a culture medium with or without the addition of hydroxycinnamic acid

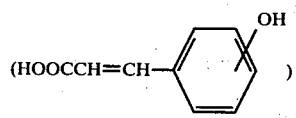

and recovering compound $I_1$ produced from the cultivated broth.

As the strains used in this invention, the actinomyces, *Streptomyces oganonensis Saito et Osono* Y-G19Z strain previously isolated and deposited as FERM-P No. 2725, ATCC No. 31167 by the inventors is suitable. When the cultivation without the addition of hydroxycinnamic acid is performed using the strain, the desired compound $I_1$ wherein $R_2$ is a sulfo group is obtained but when the cultivation with the addition of hydroxycinnamic acid is performed, the compound containing the additive is obtained. In the cultivation with the addition of hydroxycinnamic acid, other 7α-methoxycephalosporin producing strains belonging to the genus Streptomyces can be used. Typical examples of such strains are *Streptomyces griseus, Streptomyces viridochromogenes, Streptomyces fimbriatus, Streptomyces cinnamonensis, Streptomyces chartreusis,* and *Streptomyces lactamdurans* (U.S. Pat. No. 3,914,157 and Belgian Pat. No. 764,160 regarding these strains), *Streptomyces lipmanii* (U.S. Pat. No. 3,719,563), *Streptomyces clavuligerus* (U.K. Pat. No. 1,315,177), *Streptomyces wadayamensis* (U.K. Pat. No. 1,425,081), *Streptomyces jumonjinensis* (U.S. Pat. No. 3,865,693), *Streptomyces heteromorphus, Streptomyces panayensis* (U.S. Pat. No. 4,017,485), and *Streptomyces chartreusis* SF-1623 (U.S. Pat. Nos. 4,010,155 and 3,974,035).

However, the strains used in this invention are not limited to the above-described strains and any strains which belong to genus Streptomyces and produce 7α-methoxycephalosporin antibiotics may be utilized in this invention.

The cultivation is performed according to conventional cultivation method for microorganisms but submerged cultivation in a liquid culture medium is usually advantageously applied. Any culture media containing nutrients for 7α-methoxycephalosporin antibiotics producing strains belonging to the genus Streptomyces can be employed. Synthetic culture media, semi-synthetic culture media, or natural culture media are used. For the component of the culture media, there are glucose, sucrose, mannitol, glycerol, dextrin, starch, vegetable oil, etc., as the carbon source and meat extract, peptone, gluten meal, cotton seed meal, soybean meal, peanut meal, fish meal, corn steep liquor, dry yeast, yeast extract, ammonium sulfate, ammonium nitrate, urea, and other orgnaic or inorganic nitrogen sources as the nitrogen source. Also, if necessary, a metal salt such as the sulfate, nitrate, chloride, carbonate, phosphate, etc., of Na, K, Mg, Ca, Zn, Fe, etc., is added to the culture media. Still further, if necessary, a material for promoting the production of antibiotics and a defoaming agent, such as methionine, cystein, cystine, methyl oleate, lard oil, silicone oil, a surface active agent, etc., may be suitably used.

In regard to the cultivation conditions, it is generally desirable to cultivate under an aerobic condition. The cultivation temperature is preferably from about 18° C. to about 35° C., more preferably about 30° C. and good results are obtained when the pH of the culture medium is maintained at about 5 to 10, preferably about 6 to 8. The cultivation period of time depends upon the composition of the culture medium and the cultivation temperature but is generally about 3 to 10 days.

For selectively increasing the production amount of compound $I_1$, it is effective to add, for example, 4-hydroxycinnamic acid

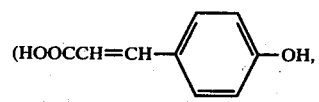

which is also called as p-coumaric acid) to the culture medium. The additive is added to the culture medium as it is or as a salt thereof in an amount of 0.1–5 mg/ml, preferably 0.5–2 mg/ml at one fell swoon prior to the cultivation or in several times at the beginning of cultivation.

For isolating the desired product of this invention from the cultivated broth, a method usually employed for isolating antibiotics from cultivated broth of microorganism is applied. Compound $I_1$ of this invention is mainly contained in the culture broth and hence after removing mycelium therefrom by centrifugal separation or filtration, the desired compound is extracted from the filtrate. That is, the desired product is separated, recovered, and purified by means generally used for isolating and recovering antibiotics, such as those utilizing differences in dissolution or solubility in suitable solvents, differences in depositing properties or depositing speeds from solutions, differences in adsorptive affinities to various adsorbents, or differences in partition between two liquid phases. These methods may be, if necessary, used individually or as a proper combination of them, or further may be repeatedly used.

The compound $I_1$ thus isolated is wholly a compound having a sulfooxycinnamoyl group

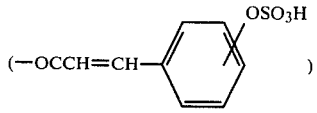

at the side chain of the 3-position of the sephalosporin nucleus. In order to obtain the corresponding compound $I_1$ having a hydroxy group from this compound, the sulfuric acid ester may be hydrolyzed by treating the compound with water-containing acetone (water content of 1-10%) with or without the addition of an acid according to known manner.

(b). The compound of formula I wherein $R_1$ is a carboxy group (HOOC—group) (hereinafter, referred to as compound $I_2$) is obtained by acting the mycelium of the D-aminoacid oxidizing enzyme producing strain belonging to the genus Trigonopsis or the treated mycelium thereof to compound $I_1$ under an aerobic condition, whereby an oxidative deamination reaction occurs to form compound $I_2$.

The strains belonging to the genus Trigonopsis used in this reaction may be selectively used from the type cultures preserved in strain preservation institutions or may be recovered from the natural world. Also, for increasing the producing activity of the compound $I_2$, mutants obtained from the above-described strains by ordinary means can be advantageously used. As the microorganisms having the aforesaid D-aminoacid oxidizing enzyme activity, there is illustrated *Trigonopsis variabilis*. This strain is available from Institute for Fermentation, Osaka, Japan as the strain number IFO-0755 or IFO-0671.

For producing compound $I_2$ using the microorganism having such a D-aminoacid oxidizing enzyme activity, it is usually preferred to first cultivate these microorganisms and acting the mycelium obtained or the treated mycelium thereof to compound $I_1$ under a proper condition. As the cultivation method for producing the mycelium, an aerobic cultivation is preferred and further a liquid cultivation with stirring under aeration is more preferred. Conventional culture media usually used for microorganisms are used in this process.

In more detail, synthetic culture media, semi-synthetic culture media, or natural culture media can be used and as the component for the culture media, glucose, sucrose, mannitol, glycerol, dextrin, starch, vegetable oil, etc., can be used as the carbon source and meat extract, peptone, gluten meal, cotton seed meal, soybean meal, peanut meal, fish meal, corn steep liquor, dry yeast, yeast extract, ammonium sulfate, ammonium nitrate, urea, and other organic or inorganic nitrogen sources are used as the nitrogen source. Also, if necessary, a metal salt such as a sulfate, nitrate, chloride, carbonate, phosphate, etc., of Na, K, Mg, Ca, Zn, Fe, etc., may be added to the culture medium. Furthermore, if necessary, a promoter for producing antibiotics and a defoaming agent such as methionine, cysteine, cystine, methyl oleate, lard oil, silicone oil, a surface active agent, etc., can be properly used.

Desirable results are obtained when the pH of the culture medium is maintained at about 3-10, preferably 4-6.

In particular, when the culture medium contains D- (or DL-) aminoacid such as D- (or DL-) methionine, D- (or DL-) alanine, D- (or DL-) valine, etc., an excellent D-aminoacid oxidizing enzyme activity is obtained. The cultivation temperature is usually 18°-37° C., preferably about 30° C. The cultivation period of time depends upon the cultivation conditions, in particular the cultivation apparatus, the composition of culture medium, the cultivation temperature, etc., but it is preferred to complete the cultivation when the D-aminoacid oxidizing enzyme activity becomes maximum and usually cultivation for 2-10 days is proper.

The mycelium thus obtained or the treated mycelium thereof is used for the D-aminoacid oxidizing reaction of compound $I_1$. In this case, the treated mycelium means (i) the mycelium which was converted into a useful form for producing the compound $I_2$ by increasing D-aminoacid oxidizing enzyme activity of the mycelium with the application of a proper treatment, (ii) D-aminoacid oxidizing enzyme, or (iii) the mycelium which was treated with fixation step to avoid the outflow of the enzyme. For example, the D-aminoacid oxidizing enzyme utilized in this invention exists in mycelium and hence the treated mycelium means (a) the activated mycelium obtained by the activation treatment of the mycelium, (b) the cell-free extract obtained by collecting D-aminoacid oxidizing enzyme producing strains from a culture medium, washing them, and applying physical or chemical means to the strains, (c) the partially purified or completely purified soluble D-aminoacid oxidizing enzyme obtained by applying a known enzyme separation and purification method to the cell-free extract, or (d) those obtained by combining the soluble enzyme to a water-insoluble polymer or an inorganic carrier by a physical or chemical means.

In this invention, the soluble enzyme described above shows a difficulty in the preparation and reuse thereof and hence is restricted in the practical use, while the activated mycelium can be recovered and reused profitably since the loss of the enzyme by outflow is less.

The activation treatment of the mycelium can be performed by giving a certain mild damage to the mycelium in such an extent of not collapsing the mycelium. Examples of the activation treatment are a method wherein the mycelium is frozen at temperatures below $-10°$ C. and at an acid pH, e.g., a pH of about 3-4 and then defrosted, a method wherein the mycelium is treated in an aqueous solution containing one or more organic solvents such as acetone, n-butanol, 2-phenylethanol, diethyl ether, cyclohexane, benzene, toluene, etc., a method wherein the mycelium is treated by 0.1-10% surface active agent, for example, a cationic surface active agent such as cetyltrimethyl ammonium halide, cetylpyridinium halide, cetyldimethylbenzylammonium halide, etc., an anionic surface active agent such as dodecyl sulfate, an alkali metal alkylarylsulfonate, sodium deoxycholate, etc., and a nonionic surface active agent such as sorbitan monolaurate, Triton X-100 (trade name), etc., in an aqueous solution, a method wherein the mycelium is treated by a diluted aqueous solution of potassium hydroxide or sodium hydroxide, or a method wherein the mycelium is suspended in a high osmotic pressure solution, for example, a 2 M cane sugar solution and then the suspension is quickly diluted with water. These activation treatments are influenced by various elements such as temperature, treating period of time, pH, the concentration of reagent, etc., and hence it is necessary to select the optimum activation conditions. The activated mycelium thus obtained may be further subjected to a fixation treatment for further reducing the outflow of the enzyme in the mycelium. This treatment is usually practiced by contacting the activated mycelium with 0.01–0.5% glutaraldehyde.

Also, when the action of catalase usually existing in a mycelium is not inhibited, the oxidative decarboxylation to compound $I_2$ becomes imperfect to form together the 7β-(5-carboxy-5-oxovaleramido)-7α-methoxycephalosporin derivative shown by general formula II

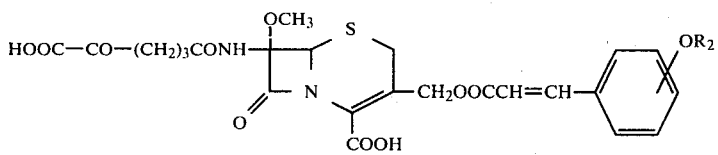

wherein $R_2$ represents a hydrogen atom or a sulfo group. Therefore, in order to obtain selectively compound $I_2$, it is desirable to inhibit the catalase activity. Examples of the proper catalase inhibitor are ascorbic acid, 3-amino-1,2,4-triazole, alkali metal azide, etc., and in particular, sodium azide is preferred. The inhibitor may be added to the reaction mixture during the conversion of compound $I_1$ to compound $I_2$ or the mycelium may be pretreated beforehand. The amount of sodium azide used for the purpose is about 1–100 mM. Furthermore, the catalase in the above-mentioned mycelium can be inactivated by heat-treating the mycelium before use for the aforesaid conversion step. That is, when the aforesaid mycelium is treated for at least 3 hours at 40°–60° C., preferably at about 50° C., the catalase activity thereof reduces remarkably but, the D-aminoacid oxidizing enzyme activity remains as it is. The heat treatment may be simply performed to the mycelium in an aqueous or buffer suspension but it is particularly convenient to subject the mycelium simultaneously to the above-mentioned heat treatment and an activation reagent treatment. For example, by applying the activation treatment to the mycelium for 4 hours at 50° C. using a solvent such as toluene, the inhibition of the catalase activity and the activation of the mycelium can be simultaneously attained.

The reaction of the enzyme system of the above-described activated mycelium with compound $I_1$ is usually performed at a pH of 6–8. It is desirable to perform the reaction at reaction temperatures of 30°–40° C. The reaction period of time mainly depends upon the potency of the enzyme but is usually 1–5 hours. Since the above enzyme reaction is performed under an aerobic condition, it is preferred to perform the reaction under aeration of air or oxygen. Also, when a small amount of hydrogen peroxide is added to the reaction system, compound $I_2$ is obtained with a good yield in a short period of time and the accompaniment with by-product of formula II does not occur.

Compound $I_2$ formed can be easily recovered by a solvent extraction or adsorption on ion exchange resin. That is, compound $I_2$ can be extracted from a reaction mixture at a pH of, e.g., 2.5 or lower using a proper organic solvent such as ethyl acetate, n-butanol, etc. Also, by combining an ion exchange resin and a solvent extraction, good results are obtained. Preferred ion exchange resin is liquid amine anion exchange resin and preferred solvents are ethyl acetate, butyl acetate, n-butanol, etc. Furthermore, the compound can be separated using a solid ion exchange resin. A proper solvent for this can be easily determined by a preliminary experiment.

Still further, in order to obtain the pure compound by purifying the product, it may be purified by a method which is usually used for the purification of antibiotics.

Compound $I_2$ can be recovered not only as the free acid but also as the alkali metal salt, alkaline earth metal salt, organic amine salt, etc.

When the side chain of the 3-position of the cephalosporin nucleus of compound $I_2$ thus obtained is a sulfuric acid esterified cinnamoyl group, the compound can be induced into the corresponding compound having a hydroxy group by treating the compound with an organic solvent solution containing or without containing an acid to hydrolyze the ester moiety thereof.

The production process of compounds of formula I of this invention was explained above and then the physicochemical properties and antibacterial activity of the novel 7α-methoxycephalosporin compounds obtained by the process are shown below.

(A).
7β-(D-5-Amino-5-carboxyvaleramido)-7α-methoxy-3-(p-sulfooxycinnamoyloxymethyl)-Δ³-cephem-4-carboxylic acid (Compound A):

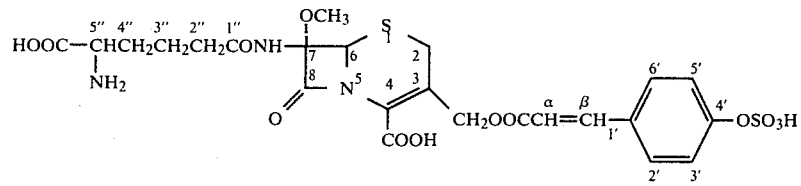

wherein the numbers attached to the side chain are added for convenience.

The physicochemical properties of the Na salt of the compound (A) are as follows:

(1) White powder.

(2) Shows no definite melting point and becomes brown at 138°–140° C.

(3) Easily soluble in water but scarcely in methanol, ethanol, ethyl acetate, butyl acetate, butanol, and other organic solvents.

(4) Amphoteric material showing ninhydrin reaction positive.

(5) Gives the ultraviolet absorption spectra shown in FIG. 1 of the accompanying drawings when measured in a 1/100 M phosphoric acid buffer solution of pH 6.5 and shows the absorption maximum at 282 nm.

(6) Gives the infrared absorption spectra shown in FIG. 2 when measured as a potassium bromide tablet and shows absorptions at 3050, 1760, 1500, 1215, 1165, 1050, 870, and 845 cm.$^{-1}$ (7) Shows the nuclear magnetic resonance spectra shown in FIG. 3 when measured using sodium 3-trimethylsilylpropionate (hereinafter, referred to as TSP) as an internal standard in heavy water and gives the following signals;
δ value (ppm):
1.90 (4H, multiplet), 2.49 (2H, multiplet), 3.34–3.67 (2H, quartet, J=18 Hz), 3.53 (3H, singlet),
3.76 (1H, multiplet, J=5.0 Hz),
5.00 (2H, quartet, J=13 Hz), 5.16 (1H, singlet),
6.43 (1H, doublet, J=16 Hz), 7.32 (2H, doublet, J=8.5 Hz), 7.61 (2H, doublet, J=8.5 Hz), 7.66 (1H, doublet, J=16 Hz).

(8) The elemental analysis after vacuum drying for 4 hours at 50° C. for $C_{24}H_{26}N_3O_{13}S_2Na \cdot 2H_2O$:

|  | C | H | N | S |
|---|---|---|---|---|
| Calculated: | 41.88% | 4.36% | 6.11% | 9.31% |
| Found: | 42.06% | 4.41% | 6.08% | 9.51% |

(9) When compound (A) was hydrolyzed for 16 hours at 100° C. with 6N-hydrochloric acid and then analyzed by means of a Hitachi 835 type high speed aminoacid analyzer, the existence of α-aminoadipic acid was confirmed.

(10) When compound (A) was hydrolyzed with Dowex 50 W (H+ type, trade name) in methanol and analyzed by a high speed liquid chromatography (using 6000A pump made by Waters Co., UV detector 280 nm, UVIDECK 100 II, made by Nippon Bunko K. K., Lichrosolve Rp 18 (trade name, made by Merck & Co., Inc.), stainless steel column of 4 mm×150 mm, solvent: mixture of methanol, acetic acid, and water (20:0.1:80 by volume ratio)), the existence of p-coumaric acid

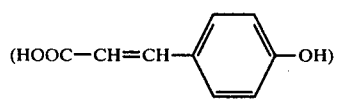

was confirmed.

Also, when the hydrolyzed product was silylated, after concentrated under reduced pressure, by BSA [N,N-bis(trimethylsilyl)acetamide] and subjected to a gas mass spectrographic analysis, the existence of the fragment of trimethylsilyl p-trimethylsilyloxycinnamate

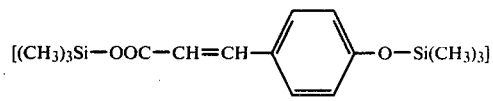

of 308 m/e was confirmed.

From the results shown above, the structure of compound (A) was determined with the existence of the 7α-methoxycephalosporin nucleus from the value of 1760 cm$^{-1}$ (cyclic lactam) in the infrared absorption spectra and the values of 3.53 ppm (3H, singlet, 7-OCH$_3$), 5.16 ppm (1H, singlet, 6-CH), 3.34–3.67 ppm (2H, quartet, J=18 Hz, 2-CH$_2$), and 5.00 ppm (2H, quartet, J=13 Hz, 3-CH$_2$) in the nuclear magnetic resonance spectra; the existence of an α-aminoadipic acid residue at the 7-position from the aminoacid analysis and further the values of signals of 1.90 ppm (4H, multiplet, 3″, 4″-CH$_2$), 2.49 ppm (2H, multiplet, 2″-CH$_2$), and 3.76 ppm (1H, multiplet, 5″-CH) in the nuclear magnetic resonance spectra; the existence of p-sulfooxycinnamic acid residue at the 3-position from (i) the values of 7.32 ppm (2H, doublet, J=8.5 Hz, 3′,5′-CH), 7.61 ppm (2H, doublet, J=8.5 Hz, 2′,6′-CH), 6.43 ppm (1H, doublet, J=16 Hz, α-CH), and 7.66 ppm (1H, doublet, J=16 Hz, β-CH) in the nuclear magnetic resonance spectra, (ii) the value of the fragment of 308 m/e in the mass spectra of the silylated product of compound (A) hydrolyzed with Dowex 50W (H+ type, trade name) in methanol, (iii) existence of two S atoms from the result of elemental analysis, and (iv) the absorptions at 870 cm$^{-1}$ (stretching vibration of S-O), 1050 cm$^{-1}$ (stretching vibration of S=O), and about 1215 cm$^{-1}$ (stretching vibration of SO$_2$) in the infrared absorption spectra.

(B). 7β-(4-Carboxybutyramido)-7α-methoxy-3-(p-sulfooxycinnamoyloxymethyl)-Δ$^3$-cephem-4-carboxylic acid (Compound B):

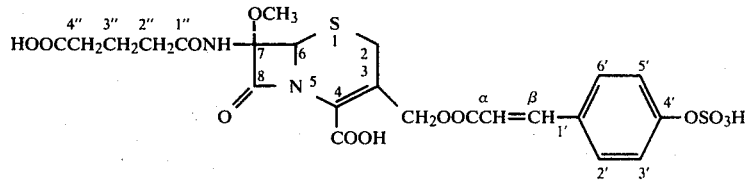

Elemental analysis of compound (B) for $C_{23}H_{23}N_2S_2O_{13}Na \cdot 2\frac{1}{2}H_2O$:

|  | C | H | N | S |
|---|---|---|---|---|
| Calculated: | 41.38% | 4.23% | 4.20% | 9.60% |
| Found: | 41.34% | 4.10% | 4.09% | 9.46% |

The physicochemical properties of the Na salt of compound (B) are as follows:
(1) White powder.
(2) Shows no definite melting point and becomes brown at 150°–160° C.
(3) Easily soluble in water but scarcely soluble in methanol, ethanol, ethyl acetate, butyl acetate, n-butanol, and other organic solvents.
(4) Acid material showing ninhydrin reaction negative.
(5) Gives the ultraviolet absorption spectra having the absorption maximum at 282 nm as shown in FIG. 4 when measured in a 1/100 M phosphoric acid buffer solution of pH. 6.5.

(6) Gives the infrared absorption spectra shown in FIG. 5 when measured as a potassium bromide tablet and shows absorptions at 3450, 1760, 1600, 1405, 1220, 1050, 868, and 845 cm.$^{-1}$ (7) Shows the nuclear magnetic resonance spectra shown in FIG. 6 when measured in heavy water using TSP as an internal standard and give the following signals:

δvalue (ppm):

1.95 (2H, multiplet), 2.44 (4H, multiplet), 3.36–3.73 (2H, quartet, J=18 Hz), 3.55 (3H, singlet), 4.93 (2H, doublet, J=13 Hz), 5.19 (1H, singlet), 6.54 (1H, doublet, J=16 Hz), 7.35 (2H, doublet, J=8.5 Hz), 7.71 (2H, doublet, J=8.5 Hz), and 7.75 (1H, doublet, J=16 Hz).

(8) When compound (B) was hydrolyzed in 6 N hydrochloric acid for 2.5 hours at 100° C., extracted with ethyl ether, evaporated to dryness, silylated with BSA, and then analyzed by mass spectrograph, it was confirmed that the fragment of bis(trimethylsilyl) glutarate of 276 m/e existed and the compound contained glutaric acid.

(9) When compound (B) was hydrolyzed by Dowex 50W (H$^+$ type, trade name) in methanol, the existance of p-coumaric acid was confirmed as in the case of compound (A).

From the results shown above, the structure of compound (B) was determined with the existence of the 7α-methoxycephalosporin nucleus from the value of 1760 cm$^{-1}$ (cyclic lactam) in the infrared absorption spectrum and the values of 3.55 ppm (3H, singlet, 7-OCH$_3$), 5.19 ppm (1H, singlet, 6-CH), 3.36–3.73 ppm (2H, quartet, J=18 Hz, 2-CH$_2$), and 4.93 ppm (2H, quartet, J=13 Hz, 3-CH$_2$) in the nuclear magnetic resonance spectra; the existence of the 4-carboxybutyramido group at the 7-position from the values of 1.95 ppm (2H, multiplet, 3″-CH$_2$), and 2.44 ppm (4H, multiplet, 2″,4″-CH$_2$) in the nuclear magnetic resonance spectra and the fragment of 276 m/e in the mass spectra of the silylated product of compound (B) hydrolyzed by hydrochloric acid; and the existence of the p-sulfooxycinnamic acid residue at the 3-position from the values of 7.35 ppm (2H, doublet, J=8.5 Hz, 3′,5′-CH), 7.71 ppm (2H, doublet, J=8.5 Hz, 2′,6′-CH), 6.54 ppm (1H, doublet, J=16 Hz, α-CH), and 7.75 ppm (1H, doublet, J=16 Hz, β-CH) in the nuclear magnetic resonance spectra, the fragment of 308 m/e in the mass spectra of the silylated product of compound (B) hydrolyzed by Dowex 50 W (H$^+$ type, trade name) in methanol, and the absorptions at 868 cm$^{-1}$ (stretching vibration of S-O), 1050 cm$^{-1}$ (stretching vibration of S=O), and about 1220 cm$^{-1}$ (stretching vibration of SO$_2$) in the infrared absorption spectra.

(C).

7β-(D-5-amino-5-carboxyvaleramido)-3-(p-hydroxycinnamoyloxymethyl)-7α-methoxy-Δ$^3$-cephem-4-carboxylic acid (Compound C):

Elemental analysis of compound (C) for C$_{24}$H$_{27}$N$_3$O$_{10}$S.1½H$_2$O:

|  | C | H | N | S |
|---|---|---|---|---|
| Calculated: | 50.00% | 5.24% | 7.29% | 5.56% |
| Found: | 49.79% | 5.13% | 7.15% | 5.42% |

The physicochemical properties of the Na salt of compound (C) are as follows:

(1) White powder.

(2) Shows no definite melting point and becomes brown at 145°–150° C.

(3) Easily soluble in water but scarcely soluble in methanol, ethanol, butyl acetate, ethyl acetate and other organic solvents.

(4) Amphoteric material showing ninhydrin reaction positive.

(5) Gives the ultraviolet absorption spectra having the absorption maximum at 307.5 nm as shown in FIG. 7 when measured in a 1/100 M phosphoric acid buffer solution of pH 6.5.

(6) Gives the infrared absorption spectra shown in FIG. 8 when measured as a potassium bromide tablet and shows absorptions at 3200, 1765, 1600, 1510, 1405, 1255, 1170 and 836 cm.$^{-1}$ (7) Gives the nuclear magnetic resonance spectra shown in FIG. 9 when measured in heavy water using TSP as an internal standard and shows the following signals:

δvalue (ppm):

1.88 (4H, multiplet), 2.50 (2H, multiplet), 3.35–3.73 (2H, quartet, J=18 Hz), 3.54 (3H, singlet), 3.76 (1H, multiplet), 4.92 (2H, quartet, J=13 Hz), 5.19 (1H, singlet), 6.41 (1H, doublet, J=16 Hz), 6.94 (2H, doublet, J=8.5 Hz), 7.59 (2H, doublet, J=8.5 Hz) and 7.71 (1H, doublet, J=16 Hz).

(8) Elemental analysis of the compound after vacuum drying for 4 hours at 50° C. for C$_{24}$H$_{26}$N$_3$O$_{10}$SNa.2-H$_2$O:

|  | C | H | N | S |
|---|---|---|---|---|
| Calculated: | 47.45% | 4.94% | 6.92% | 5.27% |
| Found: | 46.15% | 4.81% | 6.81% | 5.42% |

(9) After hydrolyzing compound (C) with 6 N-hydrochloric acid for 16 hours at 100° C., the existence of α-aminoadipic acid was confirmed as in the case of compound (A).

(10) When compound (C) was hydrolyzed with Dowex 50 W (H$^+$ type, trade name) in methanol, the existence of p-coumaric acid

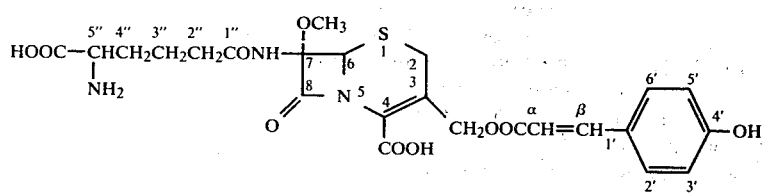

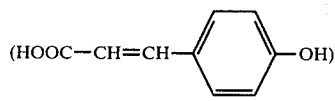

was confirmed as in the case of compound (A).

From the results shown above, the structure of compound (C) was determined with the existence of the 7α-methoxycephalosporin nucleus from the value of 1765 cm$^{-1}$ (cyclic lactam) in the infrared absorption spectrum and the values of 3.54 ppm (3H, singlet, 7-OCH$_3$), 5.19 ppm (1H, singlet, 6-CH), 3.35–3.73 ppm (2H, quartet, J=18 Hz, 2-CH$_2$), and 4.92 ppm (2H, quartet, J=13 Hz, 3-CH$_2$); the existence of the α-aminoadipic acid residue at the 7-position from the aminoacid analysis and the values of the signals of 1.88 ppm (4H, multiplet, 3″,4″-CH$_2$), 2.50 ppm (2H, multiplet 2″-CH$_2$), and 3.76 ppm (1H, multiplet, 5″-CH); and the release of the sulfo group (—SO$_3$H) of compound (A) from (i) the values of 6.94 ppm (2H, doublet, J=8.5 Hz, 3′,5′-CH), 7.59 ppm (2H, doublet, J=8.5 Hz, 2′,6′-CH), 6.41 ppm (1H, doublet, J=16 Hz, α-CH), and 7.71 ppm (1H, doublet, J=16 Hz, β-CH) in the nuclear magnetic resonance spectra, (ii) the fragment of 308 m/e (corresponding to trimethylsilyl p-trimethylsilyloxycinnamic acid) in the mass spectra of the silylated product of compound (C) hydrolyzed by Dowex 50W (H+ type, trade name) in methanol, (iii) the existence of one S atom from the results of the elemental analysis, and (iv) the vanishment of the absorptions of 870 cm$^{-1}$ (stretching vibration of S—O), 1045 cm$^{-1}$ (stretching vibration of S=O), and about 1215 cm$^{-1}$ (stretching vibration of SO$_2$) of compound (A) in the infrared absorption spectra.

(D).
7β-(4-carboxybutyramido)-3-(p-hydroxycinnamoyloxymethyl)-7α-methoxy-Δ$^3$-cephem-4-carboxylic acid (Compound D):

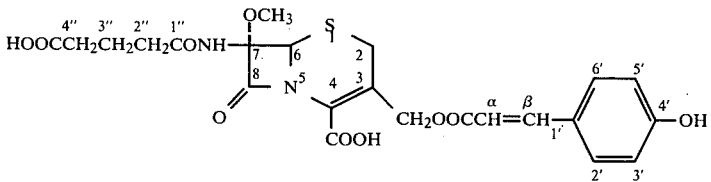

Elemental analysis of compound (D) for C$_{23}$H$_{24}$N$_2$SO$_{10}$·H$_2$O:

|  | C | H | N | S |
|---|---|---|---|---|
| Calculated: | 51.30% | 4.87% | 5.20% | 5.95% |
| Found: | 51.33% | 4.79% | 5.07% | 6.01% |

The physicochemical properties of the Na salt of compound (D) are as follows:
(1) White powder.
(2) Very hygroscopic and the measurement of melting point was difficult.
(3) Easily soluble in water, slightly soluble in methanol and ethanol, but scarcely soluble in ethyl acetate, butyl acetate, n-butanol and other organic solvents.
(4) Acid material showing ninhydrin reaction negative.

(5) Gives the ultraviolet absorption spectra shown in FIG. 10 when measured in a 1/100 M phosphoric acid buffer solution of pH 6.5 and shows the absorption maximum at 307 n.m.
(6) Gives the infrared absorption spectra shown in FIG. 11 when measured as a potassium bromide tablet and shows the absorptions of 3200, 1765, 1700, 1600, 1510, 1170 and 835 cm$^{-1}$
(7) Shows the nuclear magnetic resonance spectra shown in FIG. 12 when measured in heavy water using TSP as an internal standard and gives the following signals:

δvalue (ppm):
1.94 (2H, multiplet), 2.44 (4H, multiplet), 3.36–3.74 (2H, quartet, J=18 Hz), 3.54 (3H, singlet), 4.92 (2H, quartet, J=13 Hz), 5.19 (1H, singlet), 6.40 (1H, doublet, J=16 Hz), 6.93 (2H, doublet, J=8.5 Hz), 7.58 (2H, doublet, J=8.5 Hz) and 7.71 (1H, doublet, J=16 Hz).

(8) When compound (D) was hydrolyzed with 6 N hydrochloric acid, the existence of glutaric acid was confirmed as in the case of compound (B).
(9) When compound (D) was hydrolyzed by Dowex 50W (H+ type, trade name) in methanol, the existence of p-coumaric acid was confirmed as in the case of compound (A).

From the results shown above, the structure of aforesaid compound (D) was determined with the existence of the 7α-methoxycephalosporin nucleus from the values of 3.54 ppm (3H, singlet, 7-OCH$_3$), 5.19 ppm (1H, singlet, 6-CH), 3.36–3.74 ppm (2H, quartet, J=18 Hz, 2-CH$_2$), and 4.92 ppm (2H, quartet, J=13 Hz, —CH$_2$ at the 3-side chain); the existence of the 4-carboxybutyramido group at the 7-position from the values of 1.94 ppm (2H, multiplet, 3″-CH$_2$) and 2.44 ppm (4H, multiplet, 2″,4″-CH$_2$) in the nuclear magnetic resonance spectra and the fragment of 276 m/e in the same spectra of the silylated product of compound (D) hydrolyzed with hydrochloric acid; and the existence of the p-coumaric acid at the 3-position from the values of 6.93 ppm (2H, doublet, J=8.5 Hz, 3′,5′-CH), 7.58 ppm (2H, doublet, J=8.5 Hz, 2′,6′-CH), 6.40 ppm (1H, doublet, J=16 Hz, α-CH) and 7.71 ppm (1H, doublet, J=16 Hz, β-CH) and the fragment of 308 m/e in the mass spectra of the silylated product of compound (D) hydrolyzed by Dowex 50W (H+ type, trade name) in methanol.

Then, the results of thin layer chromatography, high speed liquid chromatography and antibacterial activity on compounds (A), (B), (C) and (D) are shown below:

1. Rf values in a thin layer chromatography using fine crystalline cellulose (Avicel SF, trade name) are shown in Table 1.

TABLE 1

| Thin layer chromatography (Rf value) | | |
|---|---|---|
|  | A* | B** |
| Compound (A) | 0.39 | 0.55 |
| Compound (B) | 0.64 | 0.84 |
| Compound (C) | 0.65 | 0.64 |
| Compound (D) | 0.89 | 0.93 |

TABLE 1-continued

| | Thin layer chromatography (Rf value) | |
|---|---|---|
| | A* | B** |
| Y-G19Z-G | 0.38 | 0.37 |
| Y-G19Z-GG | 0.74 | 0.79 |

(Note 1):
Developing solvent (by volume ratio)
A*: n-butanol:acetic acid:water (4:1:2)
B**: isopropanol:water (7:3)
(Note 2):
The detection was performed using ninhydrin or ultraviolet absorption (Manasulu light, 2536 Å).
(Note 3):
Control substance Y-G19Z-G is 7-(5-amino-5-carboxyvaleramido)-7-methoxy-3-(1-methyl-1H-tetrazol-5-yl)thiomethyl-Δ³-cephem-4-carboxylic acid described in Japanese Pat. Publication (Unexamined) No. 79,081/'77 and Y-G19Z-GG is 7-(4-carboxybutyramido)-7-methoxy-3-(1-methyl-1H-tetrazol-5-yl)thio-methyl-Δ³-cephem-4-carboxylic acid described in Japanese Pat. Publication (Unexamined) No. 15,494/'78.

2. The elution times in a high speed liquid chromatography are as follows:

TABLE 2

| High speed liquid chromatography | |
|---|---|
| | Elution time |
| Compound (A) | 2 min. 46 sec. |
| Compound (B) | 5 min. 42 sec. |
| Compound (C) | 30 min. 00 sec. |
| Compound (D) | 89 min. 18 sec. |
| Y-G19Z-G | 2 min. 14 sec. |
| Y-G19Z-GG | 4 min. 35 sec. |

Pump: 6000 A (made by Waters Co.)
Detector: UVIDEK 100 II UV Detector (made by Nippon Bunko K. K.) 280 n.m.
Column: Stainless steel column of 4 mm = 150 mm packed with Lichrosolve RP.18 (Merck & Co., Inc.)
Developing solvent: acetonitrile:acetic acid:water (10:0.2:90 by volume ratio)
Flow rate: 1 ml/min.
Pressure: 1800 P.S.I.
Column temperature: 30° C.

3. The antibacterial activities to *Proteus mirabilis* and *Salmonella gallinarum* are as follows:

TABLE 3

| | Antibacterial activity | | |
|---|---|---|---|
| | Concentn. (γ/ml) | Proteus mirabilis | Salmonella gallinarum |
| Compound (A) | 100 | 22.3 | 17.0 |
| | 500 | 28.7 | 21.5 |
| Compound (B) | 100 | 17.6 | 14.2 |
| | 500 | 27.2 | 18.3 |
| Compound (C) | 100 | 22.0 | 15.1 |
| | 500 | 27.8 | 20.0 |
| Compound (D) | 100 | 18.0 | 11.5 |
| | 500 | 27.7 | 16.2 |
| Y-G19Z-G | 100 | 21.6 | 18.5 |
| | 500 | 27.0 | 21.5 |
| Y-G19Z-GG | 100 | ± | — |
| | 500 | 19.0 | 16.0 |

(Note):
Peptone 1%, yeast extract 0.1%, agar-agar 1%, pH 8.0, plate disc method, the numerical values are the diameters of inhibitory circles.

| | Minimum inhibitory concentration (γ/ml) | | | | | |
|---|---|---|---|---|---|---|
| | Compound of this invention | | | | Known compound | |
| Test organisms | Comp. (A) | Comp. (B) | Comp. (C) | Comp. (D) | Comp. a* | Comp. b* |
| *Bacillus subtilis* ATCC 6633 | 12.5 | 100 | 3.13 | 100 | 50 | 6.25 |
| *Staphylococcus aureus* ATCC 6538F | 100 | 100 | 50 | 50 | >100 | 100 |
| *Escherichia coli* NIHJ | 6.25 | 6.25 | 3.13 | 6.25 | 25 | 12.5 |
| *Klebsiella pnuemoniae* ATCC 10031 | 25 | 25 | 3.13 | 12.5 | 50 | 25 |
| *Salmonella typhi* H901W | 3.13 | 50 | 12.5 | 25 | 25 | 50 |
| *Salmonella enteritidis* 1891 | 6.25 | 50 | 1.56 | 25 | 25 | 12.5 |
| *Shigella boydii* IID 627 | 6.25 | 25 | 6.25 | 12.5 | 25 | 50 |
| *Proteus mirabilis* IMFOM9 | 0.78 | 12.5 | 0.78 | 6.25 | 6.25 | 6.25 |
| *Proteus vulgaris* OXK US | 0.39 | 6.25 | 0.78 | 3.13 | 1.56 | 6.25 |
| *Pseudomonas aeruginosa* NCTC 10490 | >100 | >100 | >100 | >100 | >100 | >100 |

*Comp. a: 7β-(D-5-amino-5-carboxyvaleramido)-3-(α-methoxy-p-sulfooxycinnamoyloxymethyl)-7-methoxy-3-cephem-4-carboxylic acid (one of 810A in U.S. Pat. No. 3,914,157)
*Comp. b: 7β-(D-5-amino-5-carboxyvaleramido)-3-(α-methoxy-p-hydroxycinnamoyloxymethyl)-7-methoxy-3-cephem-4-carboxylic acid (one of 810A in U.S. Pat. No. 3,914,157)

The compounds of this invention may be administered orally, rectally, or by injection such as subcutaneously, intramuscularly, or intravenously in amount of 100–5000 mg per day for an adult. The doses can be variously changed according to the condition of disease, the age, weight, and the state of the patient.

Then, the production of compounds of this invention shown by formula I will be explained in more detail by the following examples.

EXAMPLE 1

A culture medium containing 1% starch, 1% glucose, 1.5% soybean flour, 0.5% yeast extract, 0.1% dipotassium hydrogenphosphate, 0.05% magnesium sulfate, and 0.3% sodium chloride was placed in 500 ml Sakaguchi flasks at 100 ml each and sterilized at 120° C. for 20 minutes. Each medium was then inoculated with *Streptomyces oganonesis* Y-G 19 Z strain and cultivated for 48 hours at 30° C. to provide a seed cultivated broth. Apart from this, to 5 liters of culture medium containing 7% starch, 2% glutch meal, 2% soybean flour, 0.8% glycerol, 0.1% casein hydroxylsate, 0.01% ferric sulfate, 4.6 g of sodium hydroxide, and 1 ml of Adekanol (trade name) was added 500 ml of a solution containing 10 g of p-coumaric acid, the pH of which was adjusted to 7.5 by 4 N sodium hydroxide solution, and the mixture was placed in a 10 liter fermenter and sterilized for 30 minutes at 120° C. The culture medium was then inoculated with 100 ml of the seed culture prepared above and cultivated for 120 hours at 30° C. After the cultivation was completed, the cultivated broth was adjusted to pH 3.0 and Radiolite (trade name) was added and stirred.

The mixture was filtered with suction, the residue was washed with water, and the washings were combined with the filtrate to provide 5.6 liters of a filtrate. After adjusting the pH of the filtrate to 3.0 with 4 N-hydrochloric acid, the solution was passed through a column packed with one liter of Diaion HP.20 (trade name) and after washing the column with 5 liters of water, the materials adsorbed were eluted with an aqueous 30% acetone solution. Thus, the fractions showing an antibacterial activity to Proteus mirabilis were collected. The active fraction was concentrated under reduced pressure at 50° C., the pH thereof was adjusted to 3.5 with dilute hydrochloric acid, and the fraction was passed through a column packed with one liter of Amberlite IRA-68 (Cl$^-$ type, trade name) to adsorb products thereon. After washing the column with 5 liters of water, the materials adsorbed were eluted with an aqueous solution (pH 7.2) containing 1 M sodium nitrate and 0.1 M sodium acetate and the fractions showing the antibacterial activity were collected. After adjusting the pH of the fraction thus collected to 3.0, the fraction was passed through a column packed with one liter of Diaion HP.20 (trade name), the column was washed with 5 liters of water, the materials adsorbed were eluted with an aqueous 30% acetone solution, and the fractions showing antibacterial activity were collected to provide about 500 ml of a solution. The solution was concentrated under reduced pressure at 50° C. to remove acetone, and lyophilized to provide about 11 g of powder of crude compound (A).

Then, 11 g of the powder was subjected to a column chromatography using a fine crystalline cellulose (Avicel, trade name), and a mixture of n-butanol, acetic acid and water (4:1:2 by volume ratio).

The fractions containing compound (A) were collected on confirming the antibacterial activity and that the fraction showed Rf value of 0.55 by UV absorption (Manasulu light 2536 Å) and ninhydrin coloring after spotting on a thin layer plate of Avicel SF (trade name) and developing it with a mixture of isopropanol and water (7:3 by volume ratio), thereby about 150 ml of a solvent mixture containing compound (A) was obtained. To the solvent mixture was added 150 ml of toluene followed by shaking and after allowing to stand the mixture, n-butanol and toluene of the upper layer formed were removed. The lower aqueous layer containing compound (A) was concentrated under reduced pressure up to about 30 ml and then lyophilized to provide 1.36 g of dried powder.

Then, the product obtained was purified with a high speed liquid chromatography [pump: 6000 A made by Waters Co., detector: UV detector, UVIDEK 100 II 280 nm made by Nippon Bunko K. K., column: stainless steel column of 8 mm × 1 meter packed with Bondapak C$_{18}$ Poracil (trade name), solvent: acetonitrile:acetic acid:water (9:0.2:90.8 by volume ratio), flow rate: 9 ml/min, and pressure: 35 Kg/cm$^2$].

Then, 1.36 g of the aforesaid powder was dissolved in 10 ml of water, 2 ml of the solution was poured in the above-mentioned column, and the fractions containing compound (A) emerging from 24 minutes since the initiation of the elution to 44 minutes were collected. This procedure was repeated five times, the fractions were combined and concentrated under reduced pressure at 50° C. followed by lyophilization to provide 75 mg of white powder.

The powder was further dissolved in water and adsorbed on Sephadex G.10 (trade name) in a column of 1.5 cm × 50 cm. The product was developed by distilled water and the fractions containing compound (A) were collected on confirming the antibacterial activity and that the fraction showed the Rf value of 0.55 by UV absorption and ninhydrin coloring after spotting the fraction on a thin layer plate of Avicel SF and developing with a mixture of isopropanol and water (7:3 by volume ratio), and lyophilized to provide 66 mg of the white powder of pure compound (A).

EXAMPLE 2

A culture medium (pH 6.0) consisting of 20 g of glucose, 4 g of potassium dihydrogen phosphate, 1 g of magnesium sulfate 2 g of ammonium sulfate, 0.5 g of calcium chloride, 0.1 g of boric acid, 0.04 g of ammonium molybdate, 0.04 g of manganese sulfate, 0.04 g of zinc sulfate, 0.045 g of cupric sulfate, 0.025 g of ferrous sulfate, 20 meg of biotin, 2 mg of thiamine hydrochloride, 1 g of DL-methionine, and 1000 ml of water was placed in a 500 ml Erlenmeyer flask at 100 ml each, sterilized for 20 minutes at 120° C., inoculated with a *Trignopsis valiabilis* IFO-0755 strain, and then subjected to shaking cultivation for 72 hours at 30° C. After the cultivation was finished, about 100 ml of the cultivated broth was collected, subjected to centrifugal separation at 2000 r.p.m. for 30 minutes at 4° C. to collect the mycelium and the mycelium was suspended in 500 ml of a 0.1 M pyrophosphate buffer solution of pH 8.1 to provide a mycelium suspension. To the mycelium suspension was added 5 ml of Triton X-100 (trade name), the mixture was shaken for 30 minutes at 37° C. to activate the mycelium, and the activated mycelium was collected. The activated mycelium was then suspended in a 0.1 M pyrophosphate buffer solution of pH 8.1 to provide an activated mycelium liquid (D-aminoacid oxidizing enzyme).

Then, 10 mg of compound (A) prepared in Example 1 was dissolved in 10 ml of a 0.05 M pyrophosphate buffer solution of pH 7.6 and after adding thereto 2 mg of sodium azide, 0.1 ml of 0.06% hydrogen peroxide solution, and 1 ml of the aforesaid activated mycelium liquid, the mixture was shaken on a water bath of 37° C. The progress of the reaction was checked every 30 minutes by a high speed liquid chromatography [pump: 6000 A made by Waters, Co., detector: UV detector, UVIDECK 100 II 280 nm made by Nippon Bunko K. K., column: stainless steel column of 4 mm × 150 mm packed with Lichrosolve RP.18 (trade name, made by Merck & Co., Inc.), solvent: acetonitrile:acetic acid:water (10:0.2:90 by volume ratio)] to determine the end of the reaction. That is, the starting material, compound (A) showed an elution time of 2 minutes and 50 seconds and compound (B) which was oxidatively deaminated by the D-aminoacid oxidizing enzyme showed an elution time of 5 minutes and 52 seconds. The reaction was finished after about 3 hours and the activated mycelium was separated from the reaction mixture by centrifugation at 4° C. and after adjusting the pH of the supernatant to 4.0 with 1 N hydrochloric acid, the solution was concentrated under reduced pressure at 50° C. up to 2 ml.

Then, the product was purified using a high speed liquid chromatography [pump: 6000 A made by Waters Co., detector: UV detecter, UVIDECK 100 II 280 nm, made by Nippon Bunko K. K., column: stainless column of 8 mm × 1 meter packed with Bondapak C$_{18}$ Porcil, solvent: acetonitrile:acetic acid:water (10:0.2:90 by volume ratio), flow rate: 9 ml/min., pressure 35 kg/cm$^2$].

The aforesaid solution was poured in the column and the fractions containing compound (B) emerging from 18 minutes after the initiation of the elution to 28 minutes were collected. The fraction was concentrated under reduced pressure at 50° C. up to about 10 ml and lyophilized to provide 5.5 mg of the white powder of pure compound (B).

EXAMPLE 3

After dissolving 25 mg of compound (A) prepared in Example 1 in 0.5 ml of water, 45.4 ml of acetone was added to the solution, thereby the solution became white turbid, but by adding 0.2 ml of 1 N hydrochloric acid to the solution, the solution became immediately clear. The solution was allowed to stand for 2 hours at room temperature (22°–23° C.). When the solution was spotted on a thin layer plate of Avicel SF, developed by a mixture of n-butanol, acetic acid, and water (4:1:2 by volume ratio), and detected by UV absorption and ninhydrin coloring, it was confirmed that compound (A) showing the Rf value of 0.39 had been converted into compound (C) showing the Rf value of 0.65. Also, by developing the product by a high speed liquid chromatography [pump: 6000 A made by Waters Co., column: stainless steel column of 4 mm×150 mm packed with Lichrosolve RP.18, detector: UV detector, UVIDECK 100 II 280 nm made by Nippon Bunko K. K., solvent: acetonitrile:acetic acid:water (15:0.5:90 by volume ratio), flow rate: 1 ml/min], it was also confirmed that compound (A) showing an elution time of 1 minute and 38 seconds had been converted into compound (C) showing an elution time of 11 minutes and 0 second. After the reaction was over, the reaction mixture was neutralized with 0.2 ml of 1 N sodium hydroxide solution and then concentrated under reduced pressure until the volume became 2 ml.

Then, compound (C) thus obtained was purified by a high speed liquid chromatography [pump: 6000 A made by Waters Co., detector: UV detector, UVIDECK 100 II 280 nm made by Nippon Bunko K. K., column: stainless steel column of 8 mm×1 meter packed with Bondapack $C_{18}$ Poracil (trade name, made by Waters Co.), solvent: acetonitrile:acetic acid:water (15:0.5:90 by volume ratio), flow rate: 9 ml/min].

The fraction containing compound (C) emerging from 14 minutes after the initiation of the elution to 19 minutes were collected, concentrated under reduced pressure at 50° C. until the volume became about 10 ml, and after adjusting the pH thereof to 5 with 1 N sodium hydroxide solution, the concentrate was lyophilized. The powder obtained was adsorbed on Sephadex G-10 column of 1.5 cm×50 cm and eluted with disilled water. The antibacterially active fractions were spotted on a thin layer plate of Avicel SF, developed with a mixture of n-butanol, acetic acid, and water (4:1:2 by volume ratio), and the Rf value thereof was checked by UV absorption and ninhydrin coloring. The fractions having the Rf value of 0.65 were collected and lyophilized to provide 14 mg of the white powder of pure compound (C).

EXAMPLE 4

In 5 ml of a 0.05 M pyrophosphate buffer solution of pH 7.6 was dissolved 6 mg of compound (C) obtained in Example 3 and after adding thereto 1 mg of sodium azide, 0.05 ml of 0.06% hydrogen peroxide solution, and 0.5 ml of the activated mycelium suspension (containing D-aminoacid oxidizing enzyme) of the *Trigonopsis valiabilis* IFO-0755 strain obtained by the method described in Example 2, the mixture was stirred on a water bath of 37° C.

The end of the reaction was confirmed by a high speed liquid chromatography [pump: 6000 A, made by Waters Co., detector: UV detector, UVIDECK 100 II, 250 nm, made by Nippon Bunko K. K., column: stainless steel column of 4 mm×150 mm packed with Lichrosolve RP.18 (trade name, made by Merck & Co., Inc.), solvent: acetonitrile:acetic acid:water (20:0.2:80 by volume ratio), flow rate: 1 ml/min].

Compound (C) showed an elution time of 3 minutes and 22 seconds but compound (D) oxidatively deaminated by the D-aminoacid oxidizing enzyme showed an elution time of 4 minutes and 48 seconds.

Also, when compound (D) was spotted on a thin layer plate of Avicel SF, developed by a mixture of n-butanol, acetic acid, and water (4:1:2 by volume ratio) and then detected by UV absorption and ninhydrin coloring, the spot of compound (C) of the Rf value of 0.65 having UV absorption and ninhydrin coloring was not detected and the spot of compound (D) of the Rf value of 0.89 having UV absorption but no ninhydrin coloring was detected.

After the reaction was over, the reaction mixture was adjusted to pH 2.5 with 1 N hydrochloric acid solution and extracted thrice each with 5 ml of ethyl acetate. The extracts were combined, dried over anhydrous sodium sulfate, and concentrated under reduced pressure. The residue was dissolved in a small amount of distilled water and after adjusting the pH thereof to 5 with 1 N sodium hydroxide solution, the solution was lyophilized to provide 3.5 mg of the white powder of pure compound (D).

EXAMPLE 5

A culture broth was cultivated in a 20 liter fermenter by the same cultivation method as in Example 1 without adding p-coumaric acid. After the cultivation was finished, the pH of the cultivated broth was adjusted to 3.0 and Radiolite was added thereto followed by stirring. The mixture was filtered under suction and the residue was washed with water. The washings were combined with the filtrate to provide 23 liters of an aqueous solution. After adjusting the pH of the aqueous solution to 3.0 with 4 N hydrochloric acid, the solution was passed through a column packed with 3 liters of Diaion HP.20 and after washing the column with 20 liters of water, the product adsorbed was eluted with an aqueous 30% acetone solution. Then, the fraction showing antibacterial activity against *Proteus mirabilis* were collected. The active fraction was concentrated under reduced pressure at 50° C. and after adjusting the pH thereof to 3.5 with 4 N hydrochloric acid, the solution was passed through a column packed with 3 liters of Amberlite IRA-68 ($Cl^-$ type). After washing the column with 10 liters of water, the product adsorbed thereon was eluted with an aqueous solution (pH 7.2) containing 1 M sodium nitrate and 0.1 N sodium acetate, and the fraction showing the antibacterial activity were collected. After adjusting the pH thereof to 3.0, the fraction was passed through a column packed with one liter of Diaion HP.20 and after washing the column with 10 liters of water, the product was eluted with an aqueous 30% acetone solution. The fractions showing the antibacterial activity were collected to provide about 2.1 liters of an aqueous solution. The solution was concentrated under reduced pressure at 50° C. to remove acetone and then lyophilized to provide about 32 g of a crude powder.

Then, 10 g of the powder was subjected to a column chromatography using a fine crystalline cellulose column with a mixture of n-butanol, acetic acid, and water (4:1:2 by volume ratio) and eluted with the solvent mixture having the same composition as above. The fractions were spotted on a thin layer plate of Avicel SF, developed by a mixture of isopropanol and water (7:3 by volume ratio).

The fractons showing the UV absorption, ninhydrin coloring and the antibacterial activity to Proteus mirabilis were collected to provide about 500 ml of a solvent mixture solution. To the solvent mixture was added 500 ml of toluene followed by shaking, the mixture was allowed to stand and n-butanol and toluene of the upper layer formed was removed. The lower aqueous layer was concentrated under reduced pressure at 50° C. up to about 70 ml and lyophilized to provide about 3.3 g of a dry powder.

When the product was analyzed by a high speed liquid chromatography, it was confirmed that the peak which coincided with compound (A) obtained in Example 1 existed and hence the product was purified by a high speed liquid chromatography [pump: 6000 A made by Waters Co., detector: UV detector, UVIDECK 100 II, 280 nm, made by Nippon Bunko K. K., column: stainless steel column of 8 mm×1 meter packed with Bondapack $C_{18}$ Poracil, solvent: acetonitrile:acetic acid:water (7:0.3:90 by volume ratio), flow rate: 9 ml/min, column temperature: 30° C.].

Then, 3.3 g of the aforesaid powder was dissolved in 10 ml of distilled water, 2 ml of the solution was poured in the aforesaid column, and fractions containing compound (A) emerging from 66 minutes after the initiation of the elution to 94 minutes were collected. This procedure was repeated five times and the fractions were combined, concentrated under reduced pressure at 50° C., and lyophilized to provide about 70 mg of white powder. The powder was purified again using a high speed liquid chromatography [pump: 6000 A made by Waters Co., detector: UV detector, UVIDECK 100 II 280 nm, made by Nippon Bunko K. K., column: stainless steel column of 8 mm×1 meter packed with Bondapak $C_{18}$ Poracil, solvent: acetonitrile:acetic acid:water (8:0.2:92 by volume ratio), flow rate: 9 ml/min, column temperature: 10° C.].

Then, 70 mg of the aforesaid powder was dissolved in 2 ml of distilled water and the solution was poured in the aforesaid column. The fractions containing compound (A) emerging from 22 minutes after the initiation of the elution to 35 minutes were collected, concentrated under reduced pressure at 50° C. and lyophilized to provide 10 mg of white powder.

The powder was subjected to a chromatography using a column of 1.5 cm×50 cm packed with Sephadex G-10 and eluted with distilled water and the fractions containing compound (A) were collected on confirming the antibacterial activity and that the fractions showed the Rf value of 0.55 by UV absorption and ninhydrin coloring after spotting the fractions on a thin layer plate of Avicel SF and then developing with a mixture of isopropanol and water (7:3 by volume ratio), and lyophilized to provide 5.5 mg of the white powder of pure compound (A).

EXAMPLE 6

A coluture medium containing 1% starch, 1% glucose, 1.5% soybean flour, 0.5% yeast extract, 0.1% dipotassium hydrogenphosphate, 0.05% magnesium sulfate, and 0.3% sodium chloride was placed in a 500 ml of Sakaguchi flask at 100 ml each and sterilized for 20 minutes at 120° C. The culture media was inoculared with *Streptomyces oganonensis* Y-G 19 Z strain and cultivated for 48 hours at 30° C. to provide cultivated broth.

Apart from this, the aforesaid culture medium was placed in a two liter Sakaguchi flask at 400 ml each, sterilized for 20 minutes at 120° C., inoculated with 2-3% the aforesaid cultivated broth, and cultivated for 48 hours at 30° C. to provide seed culture.

Furthermore, 90 liters of other culture medium containing 7% starch, 2% gluten meal, 2% soybean flour, 0.8% glycerol, 0.1% casein hydrolysate, 0.01% ferric sulfate, 42 g of sodium hydroxide, and 10 ml of Adekanol (trade name) was placed in a 150 liter fermenter and sterilized for 30 minutes at 120° C. The medium was inoculated with 2 liters of the seed culture and cultivated for 24 hours at 30° C. Apart from this, 200 g of p-coumaric acid was dissolved in 2 liters of methanol, the solution was mixed with 8 liters of an equimolar amount of sodium hydroxide solution, and after sterilizing it for 10 minutes at 120° C., the solution was added to the medium as mentioned above after cultivating for 24 hours and the medium was further cultivated for 12 hours. After the cultivation was finished, the pH of the cultivated broth was adjusted to 3.0 and filtered by means of a filter press followed by water washing to provide 120 liters of a filtrate.

The filtrate was passed through a column packed with 22 liters of Diaion HP.20 and after washing with water, the product was eluted with an aqueous 30% acetone solution, analyzed by a high speed liquid chromatography (HPLC), and the fractions containing compound (A) were collected. Then the fraction was passed through a column packed with 6 liters of Amberlite IRA 68 ($Cl^-$ type), after washing with water, the product was eluted with a solution (pH 7.2) containing 1 M of sodium nitrate and 0.1 N of sodium acetate, the fractions were analyzed by HPLC, and the fractions of compound (A) were collected. After adjusting the pH of the fraction to 3.0, the fraction was passed through a column packed with 15 liters of Diaion HP.20 and after washing with water, the product was eluted with an aqueous 30% acetone solution, the fractions were analyzed by HPLC and the fractions of compound (A) were collected. The solution was concentrated under reduced pressure at 50° C. to provide 2.5 liters of a solution containing 95 g of compound (A).

EXAMPLE 7

A culture medium (pH 6.0) consisting of 20 g of glucose, 4 g of potassium dihydrogen phosphate, 1 g of magnesium sulfate, 2 g of ammonium sulfate, 0.5 g of calcium chloride, 0.1 g of boric acid, 0.04 g of ammonium molybdate, 0.04 g of manganese sulfate, 0.04 g of zinc sulfate, 0.045 g of cupric sulfate, 0.025 g of ferrous sulfate, 20 mcg of biotin, 2 mg of thiamine hydrochloride, 1 g of DL-methionine, and 1000 ml of water was placed in a 500 ml Erlenmeyer flask at 100 ml each, sterilized for 20 minutes at 120° C., inoculated with *Trignosis valiabilis* IFO-0755 strain, and then subjected to shaking cultivation for 72 hours at 30° C. After the cultivation was finished, about 100 ml of the cultivated broth was collected, subjected to centrifugal separation at 2000 r.p.m. for 30 minutes at 4° C. to collect the mycelium, which was suspended in 500 ml of a 0.1 M pyrophosphate buffer solution of pH 8.1 to provide a suspension of mycelium. To the mycelium suspension was added 5 ml of Triton X-100 (trade name), the mixture was shaked for 30 minutes at 37° C. to activate the mycelium, and the activated mycelium was collected and suspended in a 0.1 M pyrophosphate buffer solution of pH 8.1 to provide a liquid containing activated mycelium (D-aminoacid oxydizing enzyme).

Then, 50 g of pyrophosphoric acid was dissolved in 2.4 liters of a solution containing compound (A) prepared in Example 6 and after adjusting the pH thereof to 7.5 with a 4 N aqueous sodium hydroxide solution, 800 mg of sodium azide and 5 liters of the liquid of activated mycelium of Trignopsis valiabilis IFO-0755 strain were added to the solution. Then, after further adding thereto 10 ml of hydrogen peroxide, the mixture was stirred at 37° C. to cause reaction. The reaction product was analyzed by HPLC and after confirming that compound (A) was converted into compound (B), the pH of the reaction mixture was adjusted to 3.0 with 4 N hydrochloric acid and then the mycelium was filtered away. The filtrate was passed through a column packed with 3 liters of Diaion HP.20 and after washing with water, the product was eluted with an aqueous 25% acetone solution. The fractions were analyzed by HPLC and the fractions of compound (B) were collected. Then, the fraction was passed through a column packed with 3 liters of Dowex 50 W (H+ type), the effluent was combined with washings. The mixture was concentrated under reduced pressure at 50° C. and lyophilized.

The product was further purified using Prep LC/system 500 made by Waters Co. [column: Prepack-500/$C_{18}$, solvent: mixture of methanol and 0.01 M sodium acetate buffer solution of pH 4 (15:85 by volume ratio)].

The fractions of compound (B) were collected, passed through a column packed with 3 liters of Diaion HP.20, and after washing with water, the product was eluted with an aqueous 30% acetone solution, and the fractions were analyzed by HPLC. The fractions containing compound (B) were collected and after being concentrated under reduced pressure at 50° C., the fraction was lyophilized to provide 26 g of powder of compound (B).

Then, 100 mg of the powder of compound (B) was purified using HPLC [column: stainless steel column of 8 mm×1 meter packed with Bondapack $C_{18}$ Poracil, solvent:acetonitrile:acetic acid:water (10:0.2:90 by volume ratio)].

The fractions containing compound (B) were collected and concentrated under reduced pressure at 40° C. to remove acetonitrile. Then, the fraction was passed through a column packed with 10 ml of Diaion HP.20 and after washing with water, the product was eluted with an aqueous 30% acetone solution. The fractions containing compound (B) detected by HPLC were collected, concentrated under reduced pressure at 40° C., and lyophilized. The lyophilized product was further vacuum-dried for 4 hours at 55° C. to provide 55 mg of the white powder of pure compound (B).

EXAMPLE 8

From 2.5 liters of the solution containing compound (A) obtained in Example 6, 10 ml of the solution was separated and lyophilized. Then, the powder thus formed was dissolved in 2 ml of water and 200 ml of acetone was added to the solution, thereby the solution became white turbid, but the solution became clear by adding 0.6 ml of concentrated hydrochloric acid. After confirming that compound (A) had been converted into compound (C) by the analysis with HPLC, the pH of the solution was adjusted to 2 with 4 N sodium hydroxide solution and filtered with a glass filter. The filtrate was concentrated under reduced pressure at 40° C. and lyophilized to provide 300 mg of powder.

Then, the product was further purified using HPLC [column: stainless steel column of 8 mm×1 meter packed with Bondapack $C_{18}$ Poracil, solvent:methanol:acetic acid:water (23:0.1:77 by volume ratio), column temperature: 20° C.].

The fractions containing compound (C) were collected and concentrated under reduced pressure at 40° C. to remove methanol. After adjusting the pH thereof to 3.0 with 4 N hydrochloric acid, the solution was passed through a column packed with 7 ml of Diaion HP.20 and after washing with water, the product was eluted with an aqueous 30% acetone solution and the fractions were analyzed by HPLC. Thus, the fractions containing compound (C) were collected, concentrated under reduced pressure at 40° C., lyophilized, and vacuum-dried for 4 hours at 55° C. to provide 55 mg of the white powder of pure compound (C).

EXAMPLE 9

One gram from 26 g of the lyophilized powder of compound (B) obtained in Example 7 was dissolved in 4.2 ml of water and then 594 ml of acetone was added to the solution, thereby the solution became white turbid, but the solution became clear by adding thereto 0.6 ml of concentrated hydrochloric acid. After confirming that compound (B) had been converted into compound (D) by HPLC, the pH of the solution was adjusted to 3 with 4 N sodium hydroxide and the mixture was filtered with a glass filter. The filtrate was concentrated under reduced pressure at 40° C. to remove acetone therefrom and mixed with 100 ml of water and 100 ml of ethyl acetate followed by shaking. The ethyl acetate layer formed was recovered, washed with 100 ml of a saturated sodium chloride solution, dried over anhydrous magnesium sulfate, and dried up under reduced pressure at 40° C.

Then, the product was purified by silica gel column chromatography.

The aforesaid powder was dissolved in a small amount of methanol and adsorbed on a column packed with 100 ml of silica gel prepared with a mixture of n-hexane and ethyl acetate (1:3 by volume ratio). The product thus adsorbed was eluted with a mixture of n-hexane and ethyl acetate (1:3 and then 1:9 by volume ratio) and after analyzing by HPLC, the fractions containing compound (D) were collected, dried up under reduced pressure, and purified by a silica gel column chromatography using the aforesaid solvent system.

That is, the dried product was dissolved in a small amount of methanol, adsorbed on a column packed with 75 ml of silica gel prepared with a mixture of n-hexane and ethyl acetate (1:3 by volume ratio), the product was then eluted with a mixture of n-hexane and ethyl acetate (1:3, 1:6 and then 1:9 by volume ratio), and after analyzing by HPLC, the pure fractions of compound (D) were collected. The fraction was concentrated under reduced pressure at 40° C. up to 3 ml and when about 5 ml of water was added to the fraction, the fraction became white turbid. The fraction was further concentrated under reduced pressure at 40° C., lyophilized, and vacuum-dried for 4 hours at 55° C. to provide 53 mg of the white powder of pure compound (D).

EXAMPLE 10

While stirring a mixture of 0.35 ml of distilled water, 0.15 ml of concentrated hydrochloric acid, and 49 ml of ethyl acetate at room temperature, 200 mg of compound (B) was added to the mixture and stirred overnight. The reaction mixture was washed twice each with 50 ml of an aqueous saturated sodium chloride solution, dried over anhydrous magnesium sulfate, and then concentrated under reduced pressure to provide 147 mg (yield of 88.0%) of crude compound (D). The product was purified using a silica gel column chromatography and a mixture of n-hexane and ethyl acetate (1:9 by volume ratio).

Nuclear magnetic resonance spectra (DMSO-D$_6$) δvalue (ppm):

1.76 (2H, 3″-CH$_2$, multiplet), 2.24 (4H, 2″, 4″-CH$_2$, multiplet), 3.36 (3H, 7-OCH$_3$, singlet), 3.52 (2H, 2-CH$_2$, quartet), 4.88 (2H, 3-CH$_2$, quartet), 5.12 (1H, 6-CH, singlet),

| 6.34 | 1H, α-CH, doublet, | |
|---|---|---|
| 7.52 | 1H, β-CH, doublet, | J = 16.0 Hz |
| 6.74 | 2H, 3′,5′-CH, doublet, | |
| 7.50 | 2H, 2′,6′-CH, doublet, | J = 8.0 Hz |

EXAMPLE 11

(a) To 18 ml of acetonitrile was added 1.488 g of compound (D) obtained in Example 10 and after adding thereto 0.4 g of 5-mercapto-1-methyltetrazole, the mixture was stirred for 22 hours at 80° C. The reaction mixture was concentrated under reduced pressure up to about 1 ml and 10 ml of ethyl acetate was added to the residue followed by stirring to form the crystals of 7β-(4-carboxybutyramido)-7α-methoxy-3-(1-methyltetrazol-5-yl)thiomethyl-Δ$^3$-cephem-4-carboxylic acid, which was recovered by filtration, washed with ethyl acetate and dried. The yield was 475 mg.

(b) The filtrate was combined with washings and after concentrating under reduced pressure, the residue was dispersed in 30 ml of methylene chloride. Then, 1.5 g of diphenyldiazomethane was added to the dispersion and the mixture was stirred overnight at room temperature. The reaction mixture was concentrated under reduced pressure, passed through a silica gel column chromatography, and the product was eluted using a mixture of n-hexane and ethyl acetate (1:1 by volume ratio). The eluates were combined and concentrated under reduced pressure to provide 581 mg of 7β-(4-carboxybutyramido)-7α-methoxy-3-(1-methyltetrazol-5-yl)thiomethyl-Δ$^3$-cephem-4-carboxylic acid bis(diphenylmethyl)ester.

EXAMPLE 12

(a) In 15 ml of acetonitrile was dissolved 520 mg of compound (D) obtained in Example 10 and after adding thereto 160 mg of 2-mercapto-5-methyl-1,3,4-thiadiazole, the mixture was heated to 80° C. for 6 hours with stirring. After the reaction was over, the reaction mixture was concentrated under reduced pressure until the volume because about 1 ml and then 20 ml of ethyl acetate was added to the residue to form 7β-(4-carboxybutyramido)-7α-methoxy-3-(5-methyl-1,3,4-thiadiazol-2-yl)thiomethyl-Δ$^3$-cephem-4-carboxylic acid, which was recovered by filtration, washed with ethyl acetate, and dried. The amount thereof was 34 mg.

Nuclear magnetic resonance spectra (DMSO-D$_6$): δvalue (ppm):

1.76 (2H, 3″-CH$_2$, multiplet), 2.24 (4H, 2″, 4″-CH$_2$, multiplet), 2.66 (3H, CH$_3$ of thiadiazole, singlet), 3.36 (3H, 7-OCH$_3$, singlet), 3.56 (2H, 2-CH$_2$, quartet), 4.32 (2H, 3-CH$_2$, quartet), 5.08 (1H, 6-CH, singlet).

(b) The above-mentioned filtrate was combined with the washings and after concentrating them under reduced pressue, the residue was dispersed in 15 ml of methylene chloride and after adding thereto 1.0 g of diphenyldiazomethane, the mixture was stirred overnight at room temperature. The reaction mixture was concentrated under reduced pressure. The residue was adsorbed on a silica gel column chromatography and the product adsorbed was eluted using a mixture of n-hexane and ethyl acetate (1:1 by volume ratio) and the eluates were combined and concentrated under reduced pressure to provide 172 mg of 7β-(4-carboxybutyramido)-7α-methoxy-3-(5-methyl-1,3,4-thiadiazol-2-yl)thiomethyl-Δ$^3$-cephem-4-carboxylic acid bis(diphenylmethyl)ester.

FIGS., 4, 5 and 6 show respectively the ultraviolet absorption spectra, infrared absorption spectra and nuclear magnetic resonance spectra of compound (B).

Figure 1:
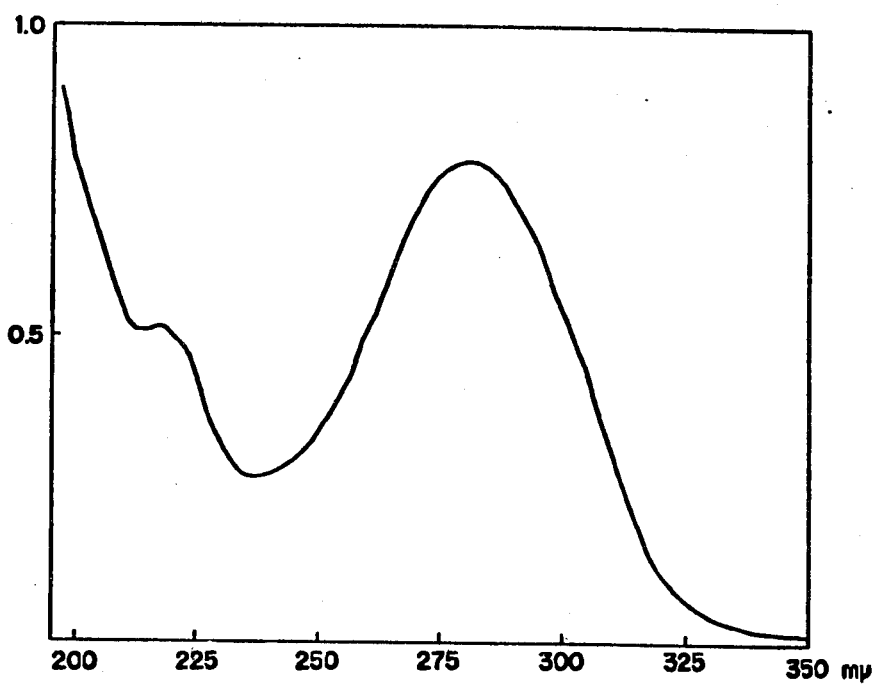
FIGS. 1, 2 and 3 show respectively the ultraviolet absorption spectra, infrared absorption spectra and nuclear magnetic resonance spectra of compound (A).
Figure 2:
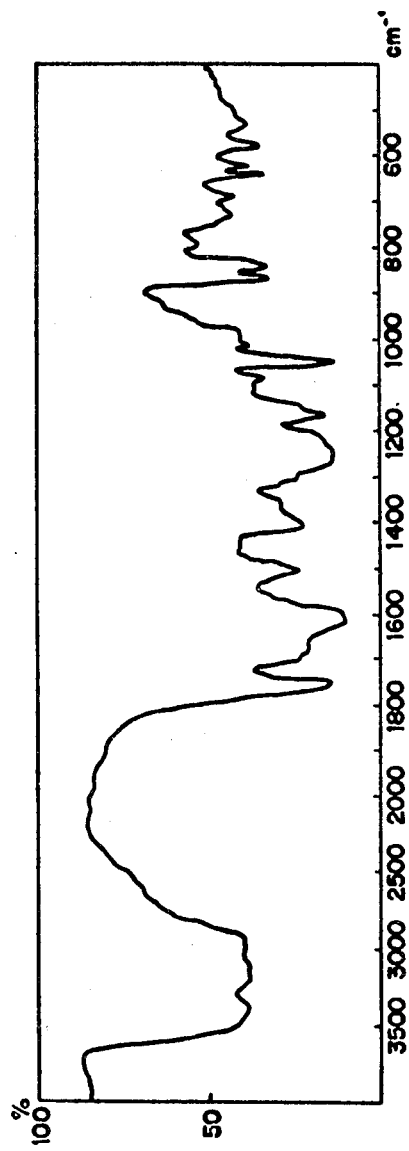
Figure 3:
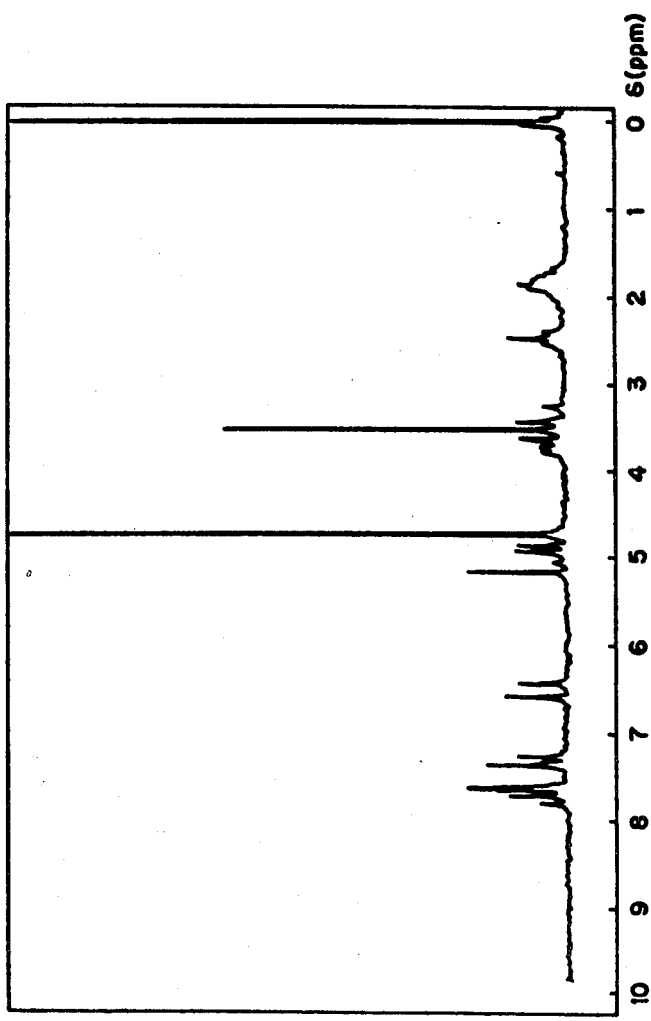
Figure 4:
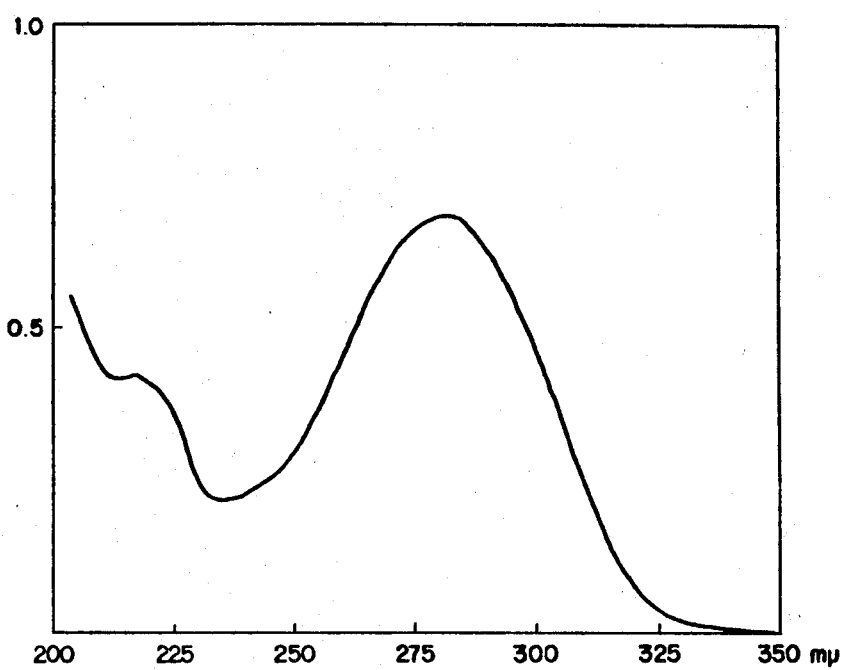
Figure 5:
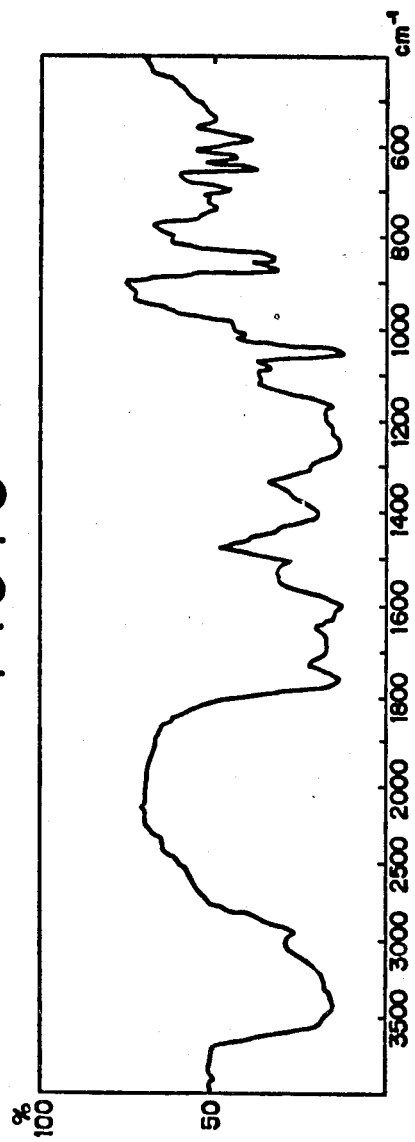
Figure 6:
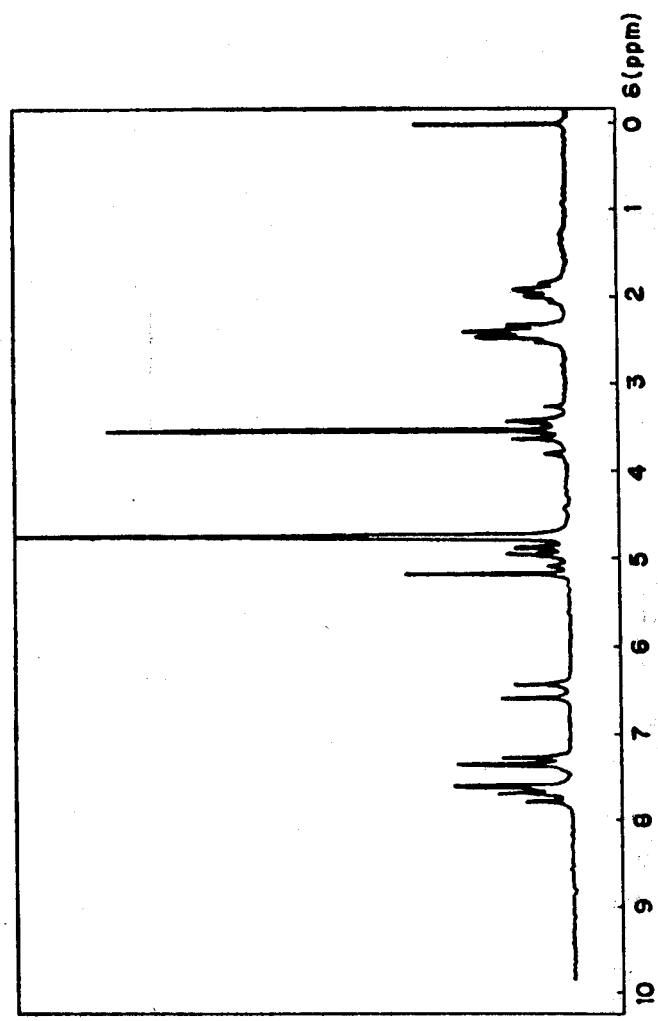
Figure 7:
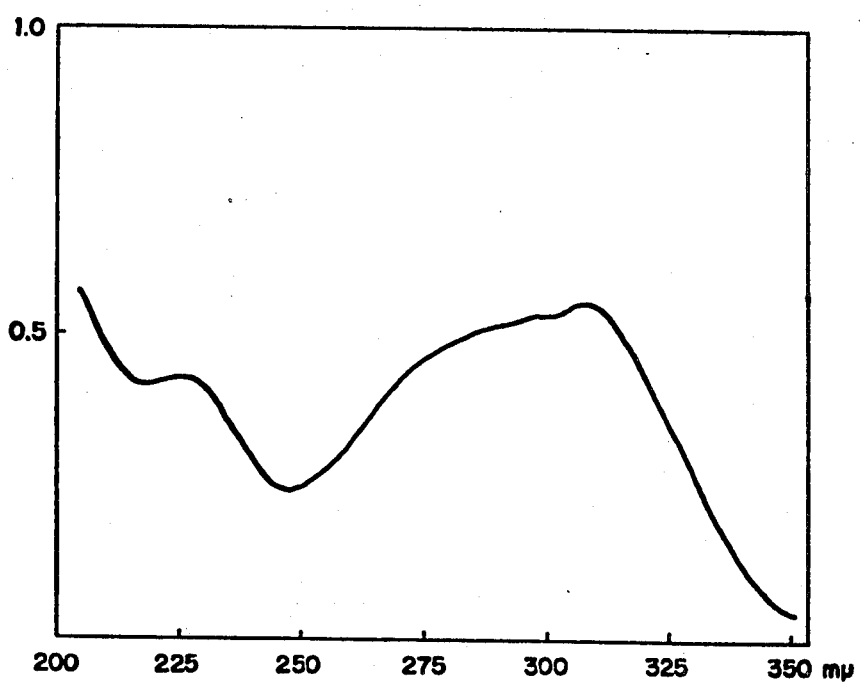
Figure 8:
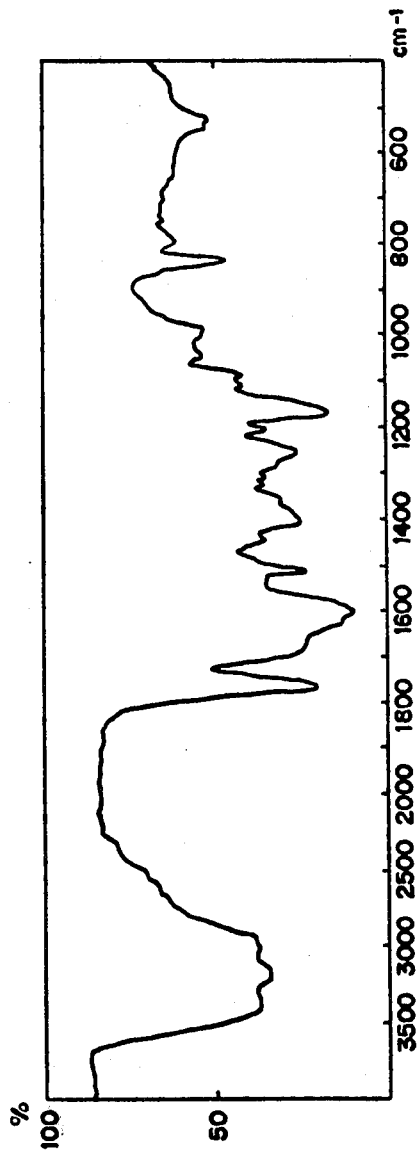
Figure 9:
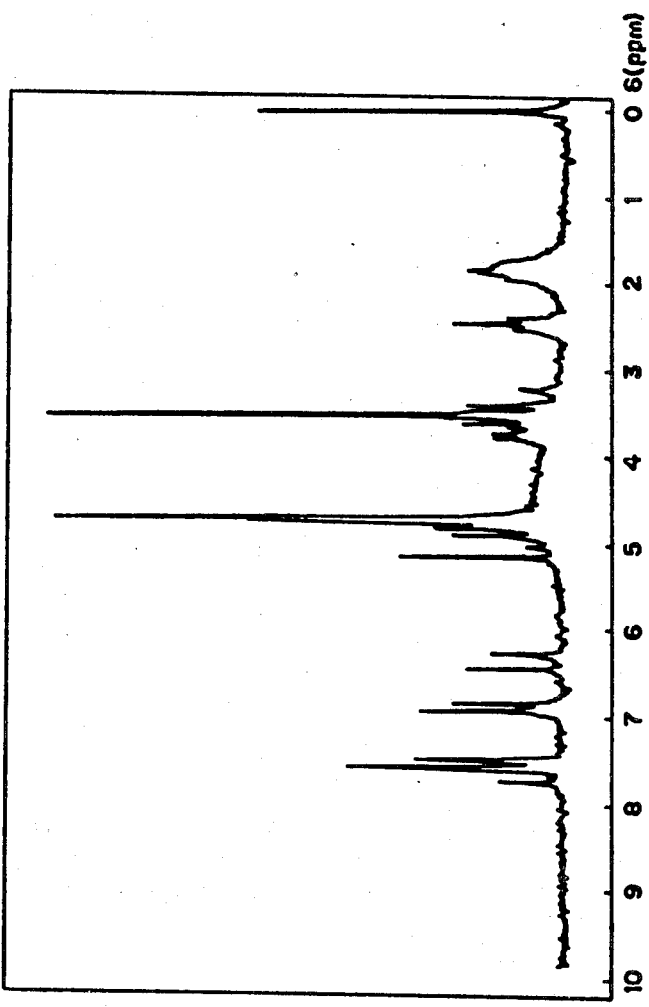

FIGS. 7, 8 and 9 show respectively the ultraviolet absorption spectra, infrared absorption spectra and nuclear magnetic resonance spectra of compound (C).

Figure 10:
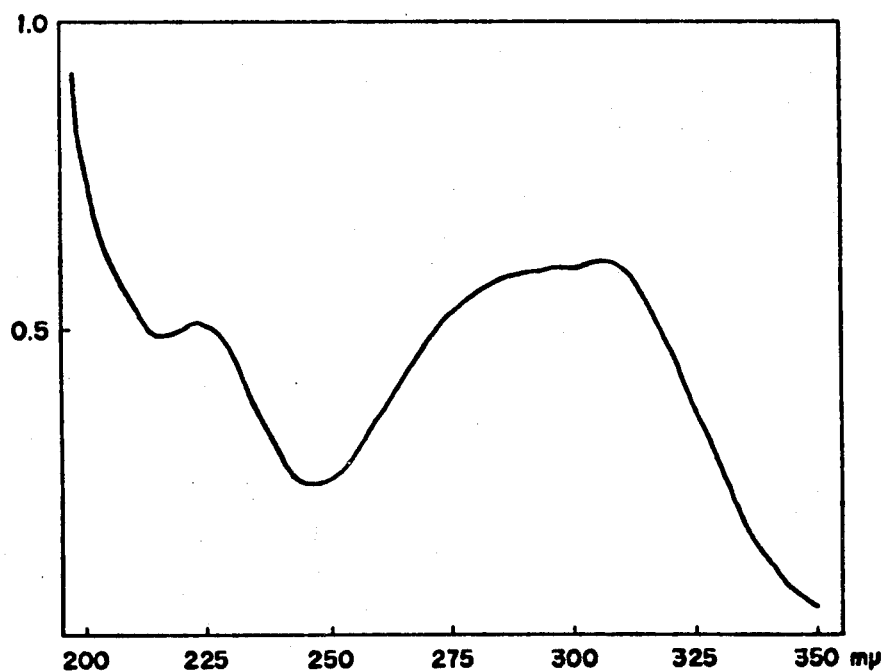
Figure 11:
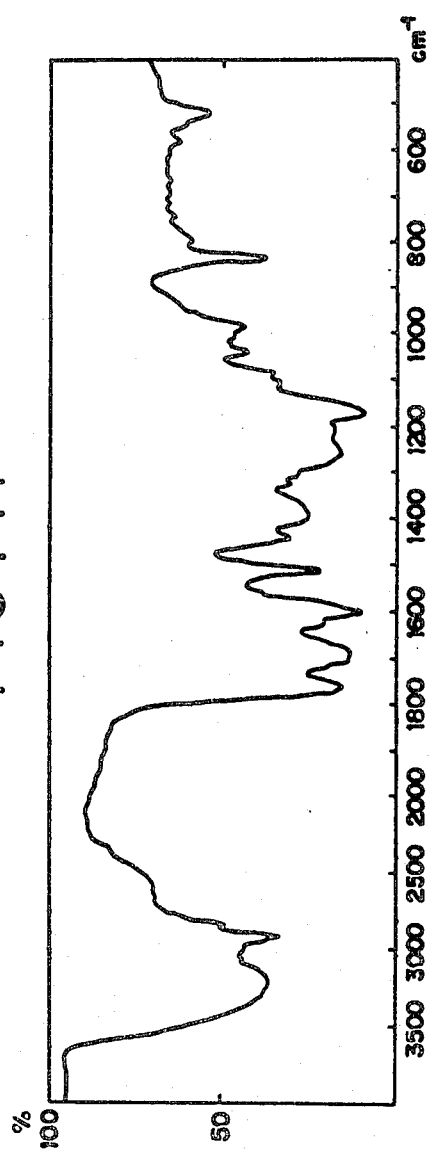
Figure 12:
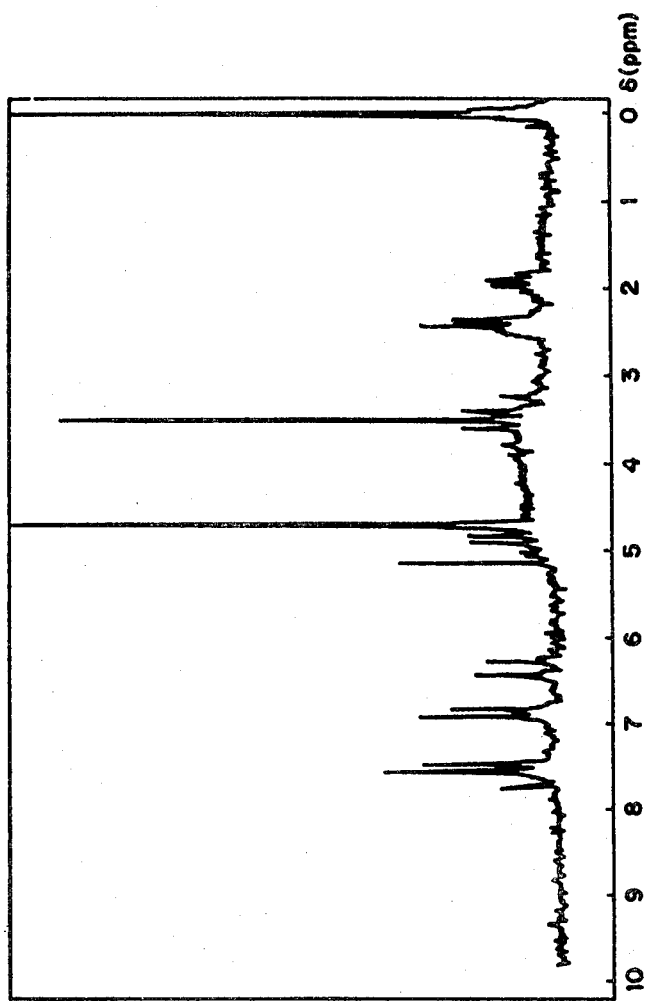

FIGS. 10, 11 and 12 show respectively the ultraviolet absorption spectra, infrared absorption spectra and nuclear magnetic resonance spectra of compound (D).

What is claimed is:

1. A process of producing the 7α-methoxycephalosporin derivative represented by the general formula $$R_1(CH_2)_3CONH-\begin{array}{c}OCH_3\\|\end{array}\begin{array}{c}S\\\end{array}$$
$$O=\!\!\!\!=\!\!\!\!N\!\!\!\!\diagdown\!\!\!CH_2OOCCH=\!\!CH-\!\!\!\!\diagup\!\!\!\!\diagdown\!\!OR_2$$
$$COOH$$

wherein R$_1$ represents a carboxy group and R$_2$ represents a sulfo group which comprises cultivating a strain belonging to the genus Streptomyces which is capable of producing the 7α-methoxy-cephalosphorin derivative shown by the formula $$HOOC-CH-(CH_2)_3-$$
$$|$$
$$NH_2$$

$$-CONH-\begin{array}{c}OCH_3\\|\end{array}\begin{array}{c}S\\\end{array}$$
$$O=\!\!\!\!=\!\!\!\!N\!\!\!\!\diagdown\!\!\!CH_2OOCCH=\!\!CH-\!\!\!\!\diagup\!\!\!\!\diagdown\!\!OSO_3H,$$
$$COOH$$

reacting the resulting product with a D-aminoacid oxidizing enzyme produced by a Trigonopsis strain capable of producing said enzyme, and recovering the thus resulting product.

2. A process as claimed in claim 1, wherein said Streptomyces strain is cultivated in the presence of hydroxycinnamic acid.

3. A process as claimed in claim 1, wherein said Trigonopsis strain is *Trigonopsis variabilis* IFO-0755 or IFO-0671.

4. A process as claimed in claim 1, further comprising hydrolyzing the —OSO₃H group to form an —OH group.

5. A process of producing the 7α-methoxycephalosporin derivative represented by the general formula

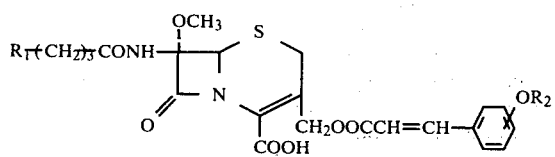

wherein R₁ represents a carboxy group and R₂ represents a sulfo group which comprises cultivating a strain belonging to the genus Streptomyces which is capable of producing the 7α-methoxycephalosporin derivative shown by the formula

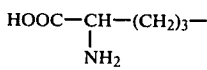

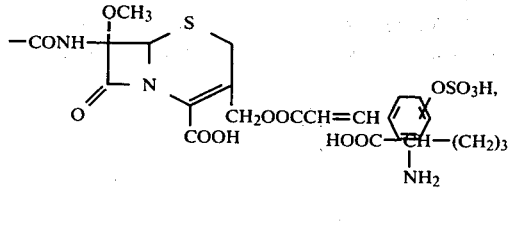

said strain being selected from the group consisting of *Streptomyces oganonensis Saito et Osono* Y-G19Z, *Strep-*

*tomyces griseus*, *Streptomyces viridochromogenus*, *Streptomyces fimbriatus*, *Streptomyces halstedii*, *Streptomyces rochei*, *Streptomyces cinnamonensis*, *Streptomyces chartreusis*, *Streptomyces lactamdurans*, *Streptomyces lipmanii*, *Streptomyces clavuligerus*, *Streptomyces wadayamensis*, *Streptomyces jumonjinensis*, *Streptomyces heteromorphus*, *Streptomyces panayensis*, and *Streptomyces chartreusis* SF-1623, reacting the resulting product with a D-aminoacid oxidizing enzyme produced by a Trigonopsis strain capable of producing said enzyme, and recovering the thus resulting product.

6. A process as claimed in claim 5, wherein said Streptomyces strain is cultivated in the presence of hydroxycinnamic acid.

7. A process as claimed in claim 5, wherein said Trigonopsis strain is *Trigonopsis variabilis* IFO-0755 or IFO-0671.

8. A process as claimed in claim 5, further comprising hydrolyzing the —OSO₃H group to form an —OH group.

9. A process as claimed in claim 5, wherein said strain is *Streptomyces oganensis Saito et Osono* Y-G19Z.

10. A process of producing the 7β-(4-carboxybutyramido)-3-(p-hydroxycinnamoyloxymethyl)-7α-methoxy-Δ³-cephem-4-carboxylic acid represented by the formula

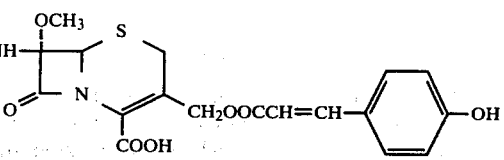

which comprises cultivating a *Streptomyces oganonensis Saito et Osono* Y-G19Z strain belonging to the genus Streptomyces in the presence of p-hydroxycinnamic acid to produce the 7β-(D-5-amino-5-carboxyvaleramido)-7α-methoxy-3-(p-sulfooxycinnamoyloxymethyl)-Δ³-cephem-4-carboxylic acid shown by the formula

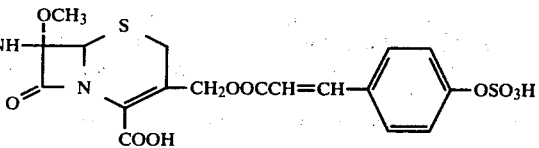

and then reacting the last-mentioned compound with a D-aminoacid oxidizing enzyme produced by Trigonopsis variabilis and hydrolyzing the —OSO₃H group to an —OH group in any desired order.

* * * * *